US011759263B2

(12) United States Patent
Yavari et al.

(10) Patent No.: US 11,759,263 B2
(45) Date of Patent: Sep. 19, 2023

(54) COLLAPSIBLE DETECTION ANTENNA FOR SURGICAL ARTICLES

(71) Applicant: Stryker Corporation, Kalamazoo, MI (US)

(72) Inventors: Fazel Yavari, Portage, MI (US);
Michael Peterson, Richland, MI (US);
Brian James Vanderwoude, Portage, MI (US); Bryan Matthew Ulmer, Grand Rapids, MI (US)

(73) Assignee: Stryker Corporation, Kalamazoo, MI (US)

( * ) Notice: Subject to any disclaimer, the term of this patent is extended or adjusted under 35 U.S.C. 154(b) by 1135 days.

(21) Appl. No.: 16/337,059

(22) PCT Filed: Sep. 28, 2017

(86) PCT No.: PCT/US2017/053930
§ 371 (c)(1),
(2) Date: Mar. 27, 2019

(87) PCT Pub. No.: WO2018/064288
PCT Pub. Date: Apr. 5, 2018

(65) Prior Publication Data
US 2020/0030039 A1     Jan. 30, 2020

Related U.S. Application Data

(60) Provisional application No. 62/400,912, filed on Sep. 28, 2016.

(51) Int. Cl.
*H01Q 7/00*     (2006.01)
*H01Q 7/02*     (2006.01)
(Continued)

(52) U.S. Cl.
CPC .............. *A61B 34/20* (2016.02); *A61B 34/76* (2016.02); *H01Q 1/2216* (2013.01); *H01Q 7/02* (2013.01);
(Continued)

(58) Field of Classification Search
CPC ......... A61B 34/20; A61B 90/98; A61B 34/76; G06K 7/10; G06K 7/10316;
(Continued)

(56) References Cited

U.S. PATENT DOCUMENTS

| 5,949,384 A | 9/1999 | Ikushima |
| 8,381,979 B2 * | 2/2013 | Franz ................. G08B 13/2411 235/462.43 |

(Continued)

FOREIGN PATENT DOCUMENTS

| CN | 1893180 A * | 1/2007 | ............ H01Q 21/28 |
| DE | 102010022086 A1 | 12/2011 | |

(Continued)

OTHER PUBLICATIONS

International Search Report for Application No. PCT/US2017/053930 dated Nov. 30, 2017, 5 pages.
(Continued)

*Primary Examiner* — Tho G Phan
(74) *Attorney, Agent, or Firm* — Howard & Howard Attorneys PLLC

(57) ABSTRACT

A collapsible detection antenna (10) to detect electromagnetic tags (12) of surgical articles (14) in an operating room (16) includes an antenna assembly (18) configured to detect the electromagnetic tags (12). The antenna assembly (18) is configured to move between a deployed configuration and a collapsed configuration. In the deployed configuration, the antenna assembly forms an antenna loop (20) configured to detect the electromagnetic tags (12). The antenna assembly
(Continued)

(18) has a greater detection range in the deployed configuration than in the collapsed configuration. The deployed configuration corresponds to a tuned shape of the antenna assembly (18) sufficient to detect the electromagnetic tags (12) in the deployed configuration.

18 Claims, 32 Drawing Sheets

(51) Int. Cl.
*A61B 34/20* (2016.01)
*A61B 34/00* (2016.01)
*H01Q 1/22* (2006.01)
*A61B 90/00* (2016.01)
*A61B 90/98* (2016.01)
*A61B 17/00* (2006.01)

(52) U.S. Cl.
CPC ..... *A61B 90/98* (2016.02); *A61B 2017/00115* (2013.01); *A61B 2017/00858* (2013.01); *A61B 2017/00862* (2013.01); *A61B 2017/00867* (2013.01); *A61B 2017/00929* (2013.01); *A61B 2017/00955* (2013.01); *A61B 2034/2051* (2016.02); *A61B 2034/2072* (2016.02); *A61B 2090/0805* (2016.02)

(58) Field of Classification Search
CPC .... G06K 7/10386; H01Q 1/12; H01Q 1/1235; H01Q 1/22; H01Q 1/2208; H01Q 1/2216; H01Q 1/2235; H01Q 7/00; H01Q 7/02
See application file for complete search history.

(56) References Cited

U.S. PATENT DOCUMENTS

| 8,786,431 | B2* | 7/2014 | Athalye | H01Q 1/44 |
| | | | | 340/572.1 |
| 9,136,597 | B2* | 9/2015 | Blair | H01Q 9/27 |
| 9,861,445 | B2* | 1/2018 | Saotome | A61B 90/98 |
| 10,461,397 | B2* | 10/2019 | Augustine | G06K 19/025 |
| 2007/0285249 | A1* | 12/2007 | Blair | A61B 5/06 |
| | | | | 340/572.3 |
| 2008/0272913 | A1 | 11/2008 | Barnes et al. | |
| 2011/0174877 | A1 | 7/2011 | Fleck et al. | |
| 2012/0212330 | A1 | 8/2012 | Halberthal et al. | |

FOREIGN PATENT DOCUMENTS

| WO | 03048810 | A2 | 6/2003 |
| WO | 2008033574 | A2 | 3/2008 |
| WO | 2011006506 | A1 | 1/2011 |

OTHER PUBLICATIONS

Machine-assisted English language abstract and machine-assisted English translation for DE 10 2010 022 086 extracted from espacenet.com database on Apr. 18, 2019, 35 pages.

* cited by examiner

COLLAPSIBLE DETECTION ANTENNA FOR SURGICAL ARTICLES

CROSS-REFERENCE TO RELATED APPLICATIONS

This application is the National Stage of International Patent Application No. PCT/US2017/053930, filed on Sep. 28, 2017, which claims priority to Provisional Patent Application No. 62/400,912, filed on Sep. 28, 2016, the contents of which are incorporated herein by reference.

TECHNICAL FIELD

The present invention relates generally to surgical articles and, more particularly to, a collapsible detection antenna to detect electromagnetic tags of surgical articles in an operating room.

BACKGROUND

It is known to provide a handheld antenna that medical practitioners have found useful for monitoring the entry of objects such as surgical articles into a surgical field and the exit therefrom and for monitoring a surgical patient to determine if any such surgical articles are within the patient.

Some detection antennas are commonly made out of hollow metal tubes. This makes the detection antenna bulky and creates challenges for storage and transportation of large antennas, especially in an operating room setting where space is a premium. In addition, the rigidity of these conventional detection antennas is a reliability concern when the detection antennas are detuned when dropped or permanently deformed. A collapsible detection antenna that overcomes these challenges is desired.

SUMMARY

Accordingly, the present invention provides a collapsible detection antenna to detect electromagnetic tags of surgical articles in an operating room including an antenna assembly configured to detect the electromagnetic tags. The antenna assembly is configured to move between a deployed configuration and a collapsed configuration. In the deployed configuration, the antenna assembly forms an antenna loop configured to detect the electromagnetic tags. The antenna assembly has a greater detection range in the deployed configuration than in the collapsed configuration. The deployed configuration corresponds to a tuned shape of the antenna assembly sufficient to detect the electromagnetic tags in the deployed configuration.

Further, the present invention provides a collapsible detection antenna to detect electromagnetic tags of surgical articles in an operating room. The collapsible detection antenna includes an antenna assembly configured to detect the electromagnetic tags. The antenna assembly is configured to move between a deployed configuration and a collapsed configuration. In the deployed configuration, the antenna assembly forms an antenna loop configured to detect the electromagnetic tags. The antenna assembly has a greater detection range in the deployed configuration than in the collapsed configuration. The deployed configuration corresponds to a tuned shape of the antenna assembly sufficient to detect the electromagnetic tags in the deployed configuration. The antenna assembly includes a loop assembly and a fabric coupled to the loop assembly. The fabric is arranged to prevent deformation of the loop assembly in at least one direction to retain a stable shape of the antenna loop when the antenna assembly is in the deployed configuration. The collapsible detection antenna further includes a housing coupled to the antenna assembly.

In addition, the present invention provides a method of collapsing a collapsible detection antenna used to detect electromagnetic tags of surgical articles. The method includes the steps of providing an antenna assembly configured to detect the electromagnetic tags. The antenna assembly is configured to move between a deployed configuration and a collapsed configuration. In the deployed configuration, the antenna assembly forms an antenna loop configured to detect the electromagnetic tags. The antenna assembly has a greater detection range in the deployed configuration than in the collapsed configuration. The deployed configuration corresponds to a tuned shape of the antenna assembly sufficient to detect the electromagnetic tags in the deployed configuration. The method also includes the steps of collapsing the antenna assembly from the deployed configuration to the collapsed configuration.

Other features and advantages of the present invention will be readily appreciated, as the same becomes better understood, after reading the subsequent description

DETAILED DESCRIPTION

Figure 1A:
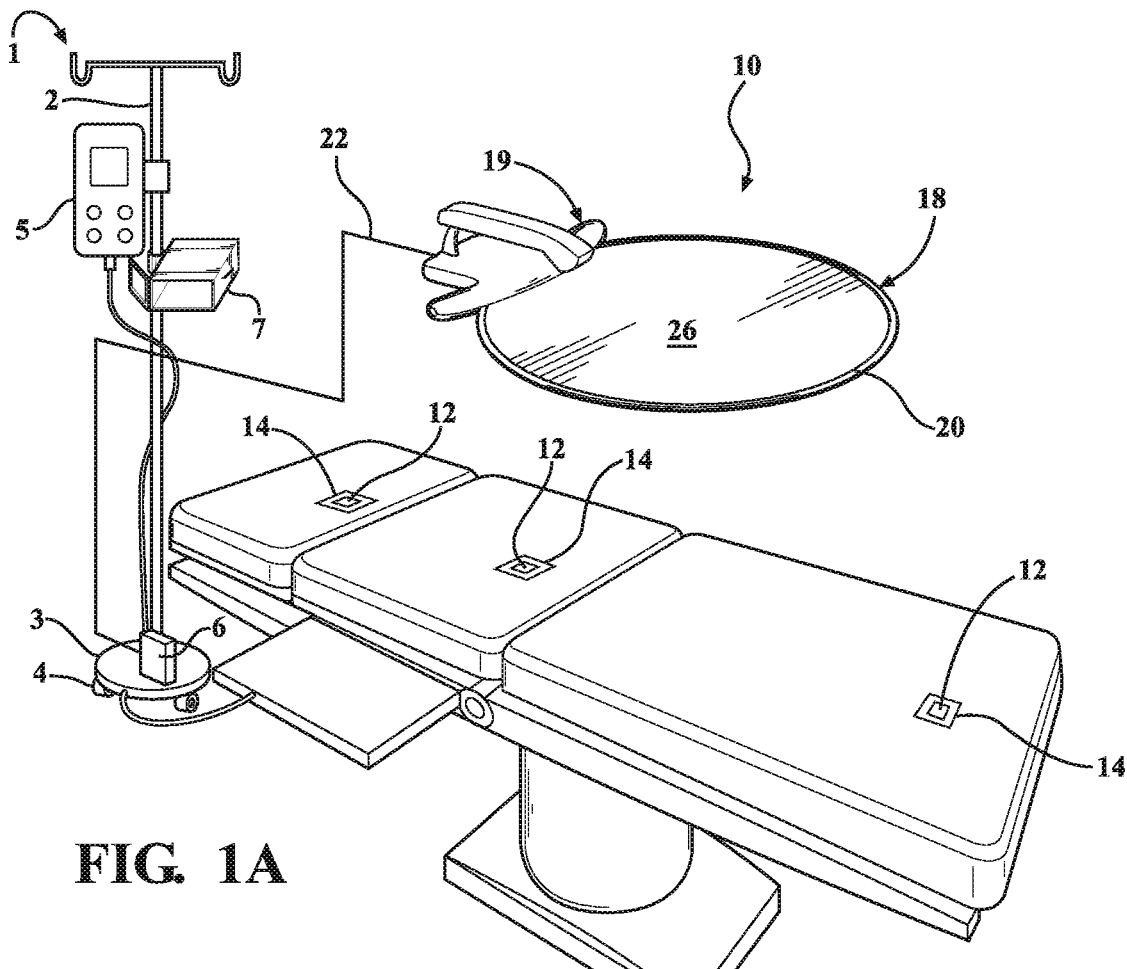
FIG. 1A is a perspective view of one embodiment of a collapsible detection antenna, according to the present invention, used to detect electromagnetic tags of surgical articles illustrated in operational relationship with a surgical operating room.

Referring to FIG. 1A, one embodiment of a collapsible detection antenna 10, according to the present invention, is shown to detect electromagnetic tags 12 of surgical articles 14 in an operating room, generally indicated at 16. The collapsible detection antenna 10 includes an antenna assembly, generally indicated at 18, configured to detect the electromagnetic tags 12. The collapsible detection antenna 10 may include a housing, generally indicated at 19, coupled to the antenna assembly 18 to support the antenna assembly 18 and configured to be grasped by a user. The antenna assembly 18 is configured to move between a deployed configuration and a collapsed configuration.

Figure 1B:
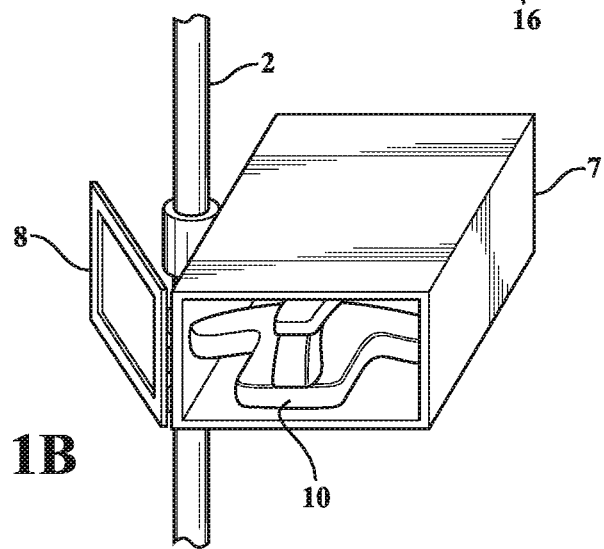
FIG. 1B is a perspective detailed view of a collapsible detection antenna shown collapsed in a storage position in relationship with the surgical operating room of FIG. 1A.
Figure 2:
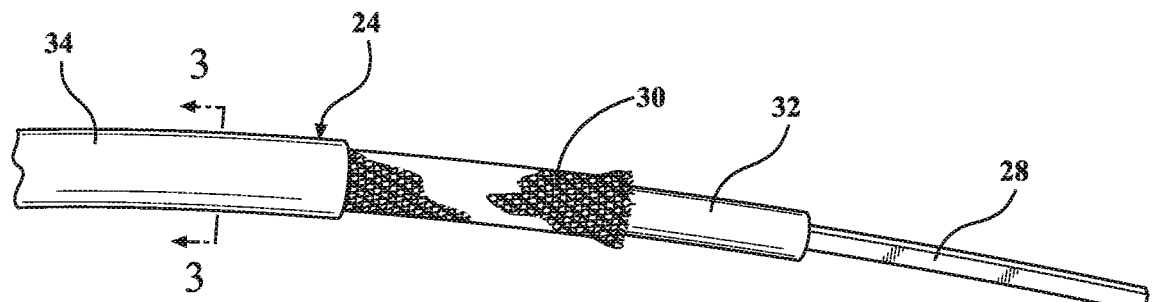
FIG. 2 is a perspective view of one embodiment of a loop assembly for an antenna assembly of the collapsible detection antenna of FIG. 1 with portions broken away.
Figure 3:
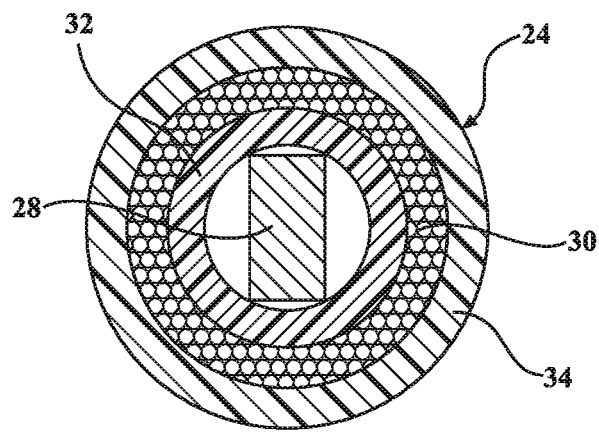
FIG. 3 is a cross-sectional view of the loop assembly of FIG. 2.
Figure 4:
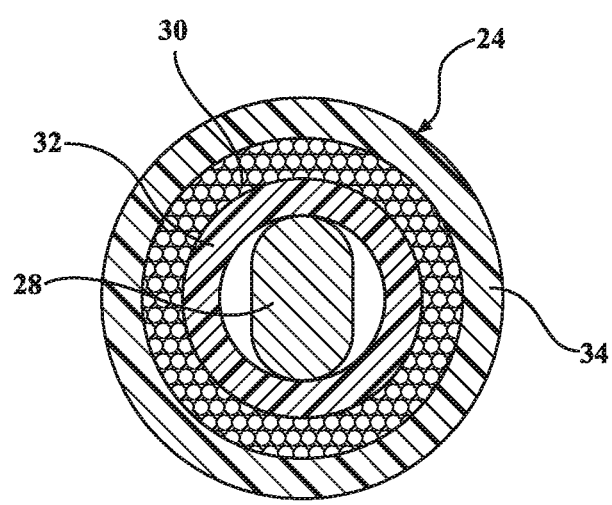
FIG. 4 is a cross-sectional view of another embodiment of the loop assembly of FIG. 2.
Figure 5:
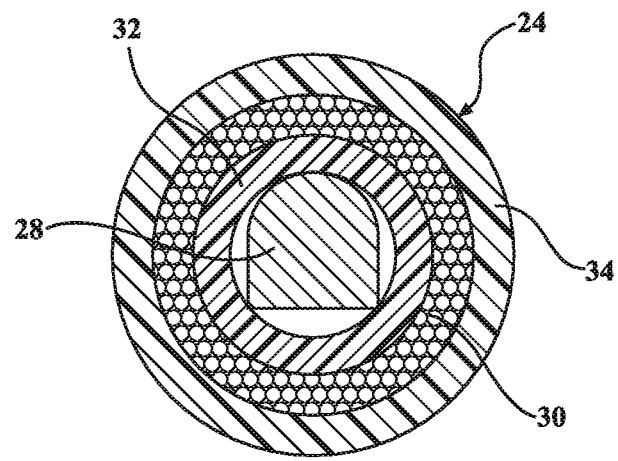
FIG. 5 is a cross-sectional view of yet another embodiment of the loop assembly of FIG. 2.

In the deployed configuration, the antenna assembly 18 forms an antenna loop 20 configured to detect the electromagnetic tags 12. In one embodiment, the antenna assembly 18 has a greater detection range in the deployed configuration than in the collapsed configuration. In some instances, the deployed configuration of the antenna assembly 18 corresponds to a tuned shape sufficient to detect the electromagnetic tags 12. As illustrated in FIG. 1, the collapsible detection antenna 10 is in the deployed configuration and the deployed configuration corresponds to a tuned shape sufficient to detect the electromagnetic tags 12. In one embodiment, the antenna loop 20 is generally circular in shape. It should be appreciated that, in one embodiment, the collapsible detection antenna 10 may be electrically energized by a wire 22 and may also serve to communicate data to and from control circuitry 6. It should also be appreciated that, in another embodiment, the collapsible detection antenna 10 may be battery powered, wireless powered, or without an external power connection. It should further be appreciated that, in one embodiment, the electromagnetic tags 12 are radio frequency (RF) tags. However, any suitable electromagnetic tag may be utilized.

In the embodiment shown in FIG. 1A, the collapsible detection antenna 10 is connected by wire 22 to control circuitry 6. Control circuitry 6 is a component of system 1, which may provide detection, counting and tracking functionality for surgical articles including an RFID tag in an operating room. The system 1 includes a support post 2 extending from a mobile base 3 supported on casters 4. The system 1 may include a unit 5 that includes a sensor having one or more antennas configured to detect electromagnetic tags. The unit 5 may also provide a user interface including a display for displaying information and one or more buttons for entering information. The unit 5 may be in communication, through a wired or wireless interface, with control circuity 6. In alternative embodiments, control circuitry 6 may be integrated into the unit 5. As shown in FIG. 1A, and in additional detail in FIG. 1B, the system 1 may include a storage container 7 for housing the collapsible detection antenna 10 in a collapsed state. The storage container 7 may be an end-loading box, having a windowed door 8, defining an interior volume sufficient to enclose the collapsible detection antenna 10. Providing a windowed door 8 allows a user to easily view whether the collapsible detection antenna 10 is present within the storage container 7, for example, at the start of a surgical procedure.

In alternative embodiments, the storage container 7 may be a top-loading box, or any other suitable configuration for containing the collapsible detection antenna 10 in convenient proximity with the system 1. In further alternative embodiments, the storage container may not be separately supported on the post 2, but may instead be integrated with another system component. For example, in an embodiment not shown, unit 5 may provide on a front side the sensor and user interface, while the back incorporates a recess for receiving the collapsible detection antenna 10 for storage.

In certain embodiments, the collapsible detection antenna 10 may be battery powered, wireless powered, or without an external power connection. In those embodiments, the storage container may further connection and interface features to the collapsible detection antenna 10 when it is placed within the storage container 7. In one embodiment, the collapsible detection antenna 10 includes a rechargeable battery with external electrical contacts. The storage container 7 may be wiredly connected to control circuitry 6 and provide within its interior complementary electrical contacts to recharge the battery of the collapsible detection antenna 10. Similarly, the storage container 7 and collapsible detection antenna 10 may be equipped for electromagnetic induction to recharge wirelessly an included battery.

The deployed configuration of the antenna assembly 18 results in the antenna assembly 18 having at least one dimension greater than when the antenna assembly 18 is in the collapsed configuration. For example, in the deployed configuration, the antenna assembly 18 may have a greater diameter than when the antenna assembly 18 is in the collapsed configuration.

The collapsible detection antenna 10 may be operated by a user (not shown) such as a medical personnel in two or three modes of operation. In one mode, the collapsible detection antenna 10 may be moved around the patient and/or the surgical field to detect the electromagnetic tags 12 of the surgical articles 14 in the operating room 16. In another mode, the collapsible detection antenna 10 may be employed to act either as an entry or exit antenna or both, thereby providing added data from the surgical articles 14 that are scanned in and out of the surgical field with an additional reading in respect of the surgical site. There are several ways in which this may be accomplished. The collapsible detection antenna 10 may operate in a default mode such that it scans the electromagnetic tags 12 of the surgical articles 14 which are being taken out of the surgical site.

The collapsible detection antenna 10 may also be employed in a contextual manner. The first time the collapsible detection antenna 10 sees a specific identifier on a specific surgical article 14, the article 14 is regarded as entering the surgical site. The second time the collapsible detection antenna 10 sees the article 14, the article 14 is regarded as exiting the surgical site. It should be appreciated that there may also be an additional user control in the form of a switch, such as a toggle switch (not shown), on the collapsible detection antenna 10 for the user to determine whether the surgical articles 14 are being scanned in or out. It should also be appreciated that the collapsible detection antenna 10 may have its detection range increased or decreased to detect the electromagnetic tags 12 of the surgical articles 14 within a predetermined distance or range.

In one embodiment illustrated in FIGS. 1-6, the antenna assembly 18 includes a loop assembly, generally indicated at 24, and a support member 26 coupled to the loop assembly 24. The loop assembly 24 and support member 26 are arranged to prevent deformation of the loop assembly 24 in at least one direction to retain a stable shape of the antenna loop 20 when the antenna assembly 18 is in the deployed configuration. In one embodiment, the support member 26 prevents deformation of the loop assembly 24 in a radial outward direction when the antenna assembly 18 is in the deployed configuration. The support member 26 is selected from the group comprising woven or non-woven fabric, thermoplastic films, or a combination thereof. The fabric may be coated on both sides of the antenna assembly 18 with polyurethane or other material in certain embodiments that may allow cleanability and/or disinfection.

Referring to FIGS. 2-6, the loop assembly 24 includes a structural member 28 and a conductor 30 disposed about the structural member 28. In one embodiment, the structural member 28 comprises spring steel. In other embodiments, the structural member 28 may be made using a creep-resistant material. In various embodiments, the creep resistant material is selected from the group consisting of PEEK, nitinol, or combinations thereof. In one embodiment illustrated in FIGS. 2, 3, and 6, the structural member 28 has a rectangular cross-sectional profile. In another embodiment illustrated in FIG. 4, the structural member 28 has an obround or oval cross-sectional profile. In yet another embodiment illustrated in FIG. 5, the structural member 28 has a semi-circular cross-sectional profile. In one embodiment, the rectangular cross-sectional profile of the structural member 28 has a height to width ratio ranging between 20:1 to 5:1. This ratio prevents the structural member 28 from being easily bent in the height direction and can only be bent in the width direction. The increased height provides structural support so that the antenna assembly 18 is not flimsy when extended and in use, while not adversely affecting the collapsibility of the antenna assembly 18. It should be appreciated that the structural member 28 provides structural support and collapsing capabilities, and may include any suitable cross-sectional profile, or suitable material. It should also be appreciated that the structural member 28 may be conductive in certain embodiments, or non-conductive in other embodiments.

In one embodiment, the conductor 30 is generally circular or annular in cross-sectional profile, but may have any suitable profile. In one embodiment, the conductor 30 may be made from a braided wire disposed about the structural member 28. In one embodiment, the braided wire is made of aluminum/copper material. In other embodiments, the conductor 30 may be provided adjacent to the structural member 28, such as along the side of the structural member 28 and coupled thereto, with adhesive, welding, or other suitable coupling means.

The loop assembly 24 may include a first layer 32 of electrical insulator disposed between the conductor 30 and the structural member 28. The loop assembly 24 may include a second layer 34 of insulation disposed about the conductor 30. In one embodiment, the first layer 32 may be formed by dipping the structural member 28 into an insulation such as rubber to form a dip coat. In other embodiments, the conductor 30 and the second layer 34 may be eliminated at a cost of lower read range and spring steel or Nitinol may be used as the RF wave-carrying antenna material. The read range would be reduced significantly due to higher resistance of the material, smaller skin effect and lower quality factor (Q) of the antenna. It should be appreciated that the conductor 30 is used as the RF-wave-carrying antenna material. It should also be appreciated that the loop assembly 24 is a multi-layer assembly that provides flexibility of the collapsible detection antenna 10 without sacrificing performance.

In one embodiment illustrated in FIGS. 7-20, the housing 19 may include a base 36 and a handle 38 coupled to the base 36 to be grasped by the user so that the antenna assembly 18 can be moved by the user. In one embodiment, the base 36 has a general "T" shape and the handle 38 has an inverted "L" shape. The base 36 includes a cavity 40 to receive a tuning board 42 (FIG. 18) to be described. The housing 19 is made of a rigid material such as plastic. It should be appreciated that the base 36 and handle 38 may have any suitable shape. It should also be appreciated that the handle 38 allows the user to move the antenna assembly 18 around the operating room 16 without having to directly touch the antenna loop 20 and hence de-tune the antenna assembly 18.

Figure 18:
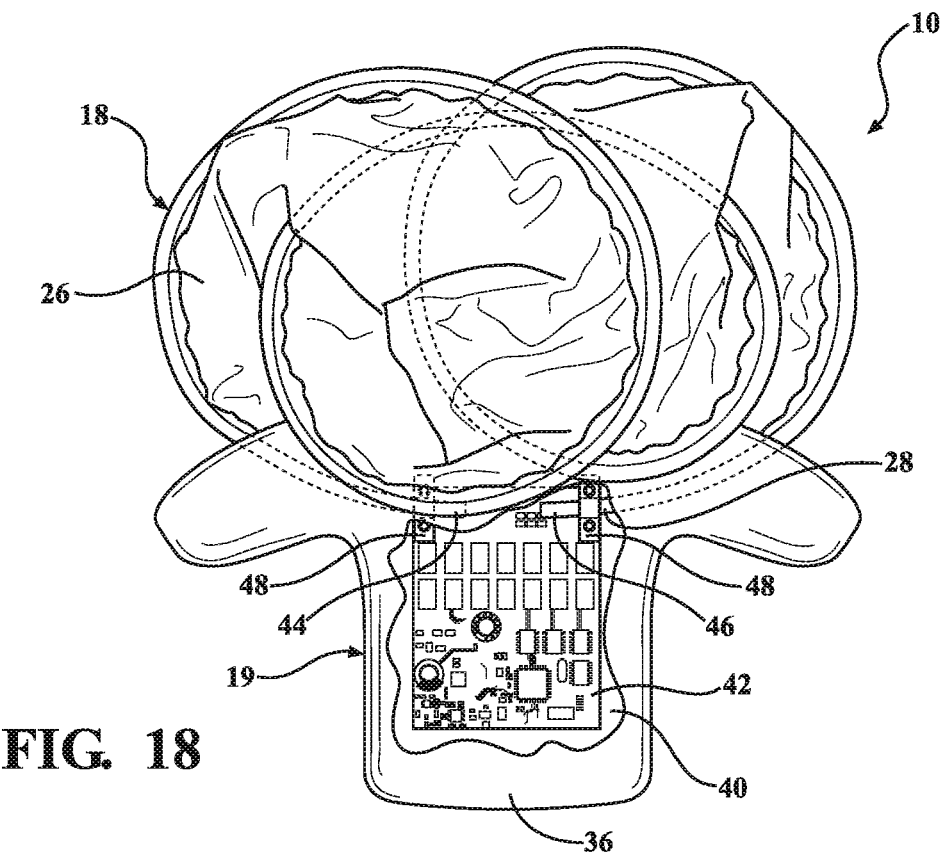
FIG. 18 is a view illustrating a fourth step of collapsing the collapsible detection antenna of FIGS. 12 and 15.

As illustrated in FIG. 18, the collapsible detection antenna 10 includes a tuning board 42 in electrical communication with the conductor 30 to generate a detection field to match a frequency range of the electromagnetic tags 12. The tuning board 42 is used to tune the antenna assembly 18 as well as communicate with and receive power from an RFID reader (not shown). In one embodiment, the tuning board 42 is disposed in the cavity 40 of the base 36 of the housing 19.

The structural member 28 has a first end 44 and a second end 46 with the first end 44 and the second end 46 coupled to the tuning board 42 and fixed relative to the base 36 of the housing 19. The collapsible detection antenna 10 may include one or more connectors 48 to attach the ends of the conductor 30 to the tuning board 42. In one embodiment, the ends of the conductor 30 and structural member 28 are clamped by the connectors 48 to the tuning board 42. It should be appreciated that the structural member 28 is not electrically connected to the tuning board 42, but mechanically held in place by the connectors 48. It should also be appreciated that, in certain embodiments, the structural member 28 is enclosed inside the conductor 30 and hence does not shield the electromagnetic field generated by AC current going through the conductor 30. It should also be appreciated that the structural member 28 is not a continuous conductive loop because the structural member 28 is cut before the structural member 28 is clamped to the tuning board 42 so no eddy currents are created. The contents of U.S. Patent Application Publication No. 2011/0174877 are hereby incorporated by reference. The '877 publication discloses exemplary tuning board configurations. The tuning board 42 may emit a signal that matches the resonant frequency of the antenna assembly 18 in the deployed configuration, but not the resonant frequency of the antenna assembly 18 in the collapsed configuration.

Figure 33:
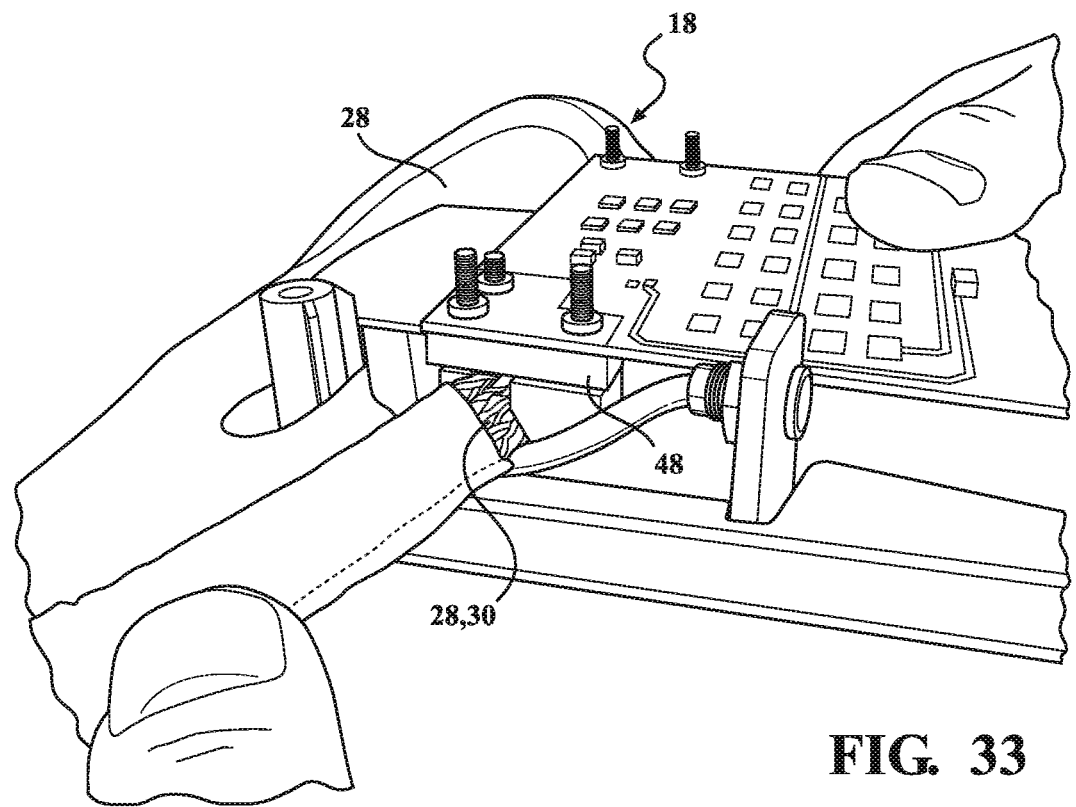
FIG. 33 is a perspective view of a portion of the collapsible detection antenna of FIG. 1 with a housing removed.
Figure 34:
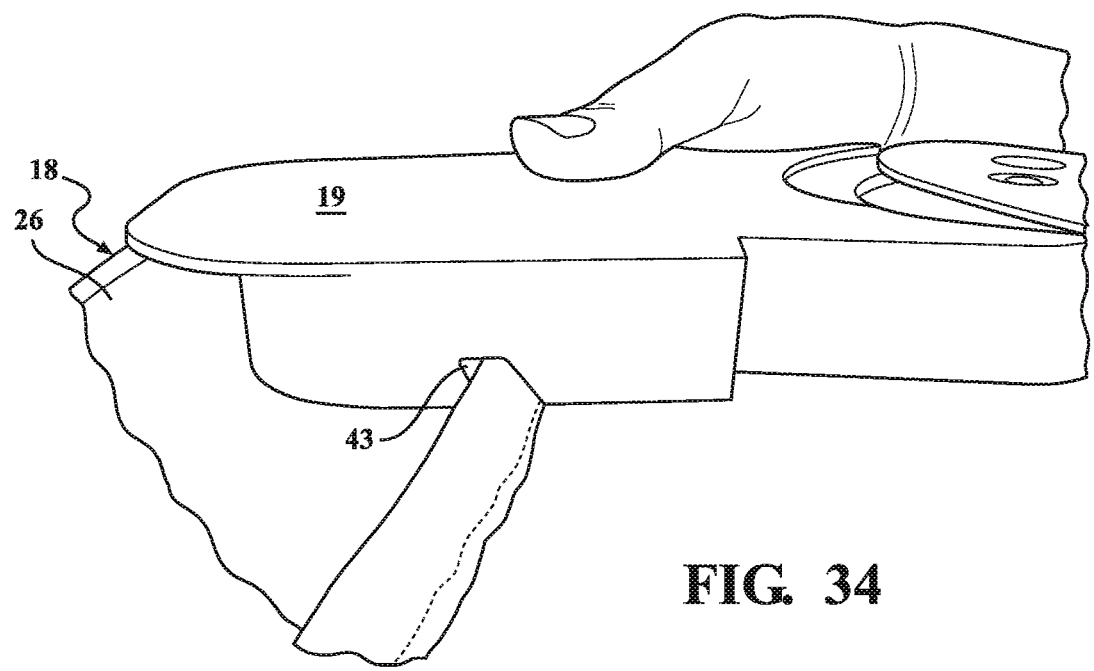
FIG. 34 is a view similar to FIG. 33 with the housing.

In another embodiment illustrated in FIGS. 33 and 34, the structural member 28, covered by the conductor 30, is twisted or bent up a predetermined amount such as approximately thirty (30) degrees at the connectors 48 to bias the sagging of the support member 26 towards the top of the antenna assembly 18. Either one or both the connector 48 and the housing 19 may include an angled or slanted slot 43 to bias the structural member 28. It should be appreciated that this bias of the structural member 28 allows gravity or weight of the antenna assembly 18 to help bring the antenna assembly 18 to a neutral position. It should be appreciated that the embodiment illustrated in FIGS. 33 and 34 is upside down to show under the housing 19.

Figure 48:
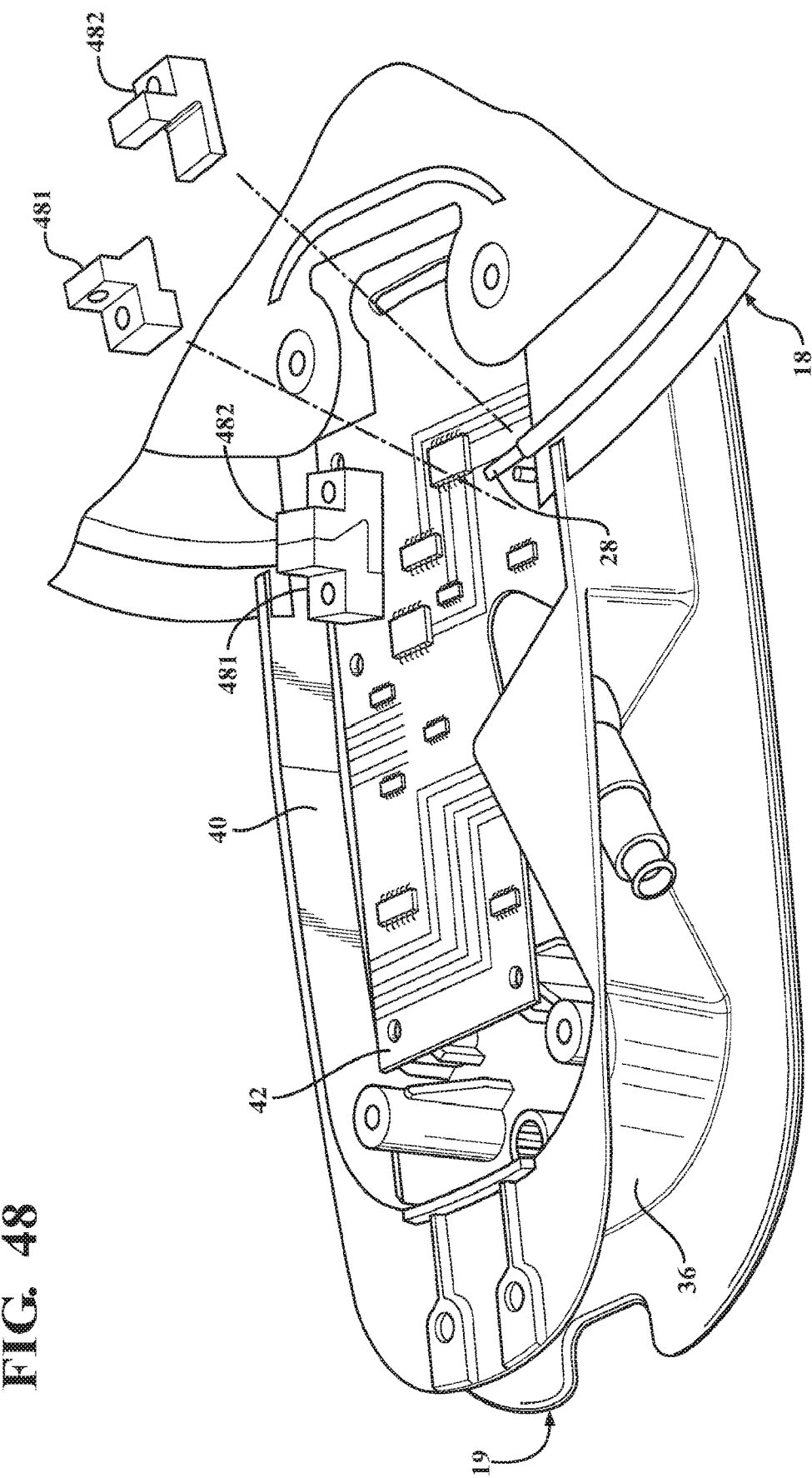
FIG. 48 is a perspective view of a portion of the collapsible detection antenna of FIG. 1 in an alternative embodiment with a housing removed.

In the embodiment shown in FIG. 48, the collapsible detection antenna 10 is shown with a portion of housing 19 to illustrate tuning board 42. In this embodiment, the structural member 28 is secured to the tuning board 42 with clamping connectors 481 and 482. The angle of the clamping surfaces of connectors 481 and 482 can retain the structural member 28 at the desired angle, for example, ranging from about 30 to about 80 degrees relative to the tuning board 42 to bias the structural member 28 to prevent sagging. In this embodiment, the ends of the structural member 28 are captured within the connectors 281 and 482. In alternative embodiments, the number and shape of connectors securing antenna assembly 18 to the tuning board may be different from the embodiment as illustrated.

In one exemplary configuration, the tuning board 42 is capable of dynamically tuning the collapsible detection antenna 10. In other words, the tuning board 42 may adjust its emitted signal to match resonant frequency of the antenna assembly 18 as environmental conditions change or as the shape of the antenna assembly 18 is adjusted. For example, the tuning board 42 may emit a different signal to the antenna assembly 18 if the antenna assembly 18 is in a square shape or a circular shape. In an alternative configuration, the tuning board 42 may be configured to dynamically adjust its emitted signal to accommodate changing environmental conditions or damage to the antenna assembly 18, but not necessarily changes in shape of the antenna assembly 18, i.e., change its signal such that the antenna assembly 18 is in resonance while the antenna assembly 18 is in the collapsed configuration. It should be appreciated that the antenna assembly 18 may have any suitable shape such as triangular, rectangular, etc.

The collapsible detection antenna 10 may be configured to detect radio frequency tags of various types and configurations. In one specific embodiment, the collapsible detection antenna 10 is configured to detect high frequency RF tags responsive to a frequency ranging from 3-30 MHz. In this embodiment, the collapsible detection antenna 10 is not configured to detect frequencies outside of this range.

Figure 7:
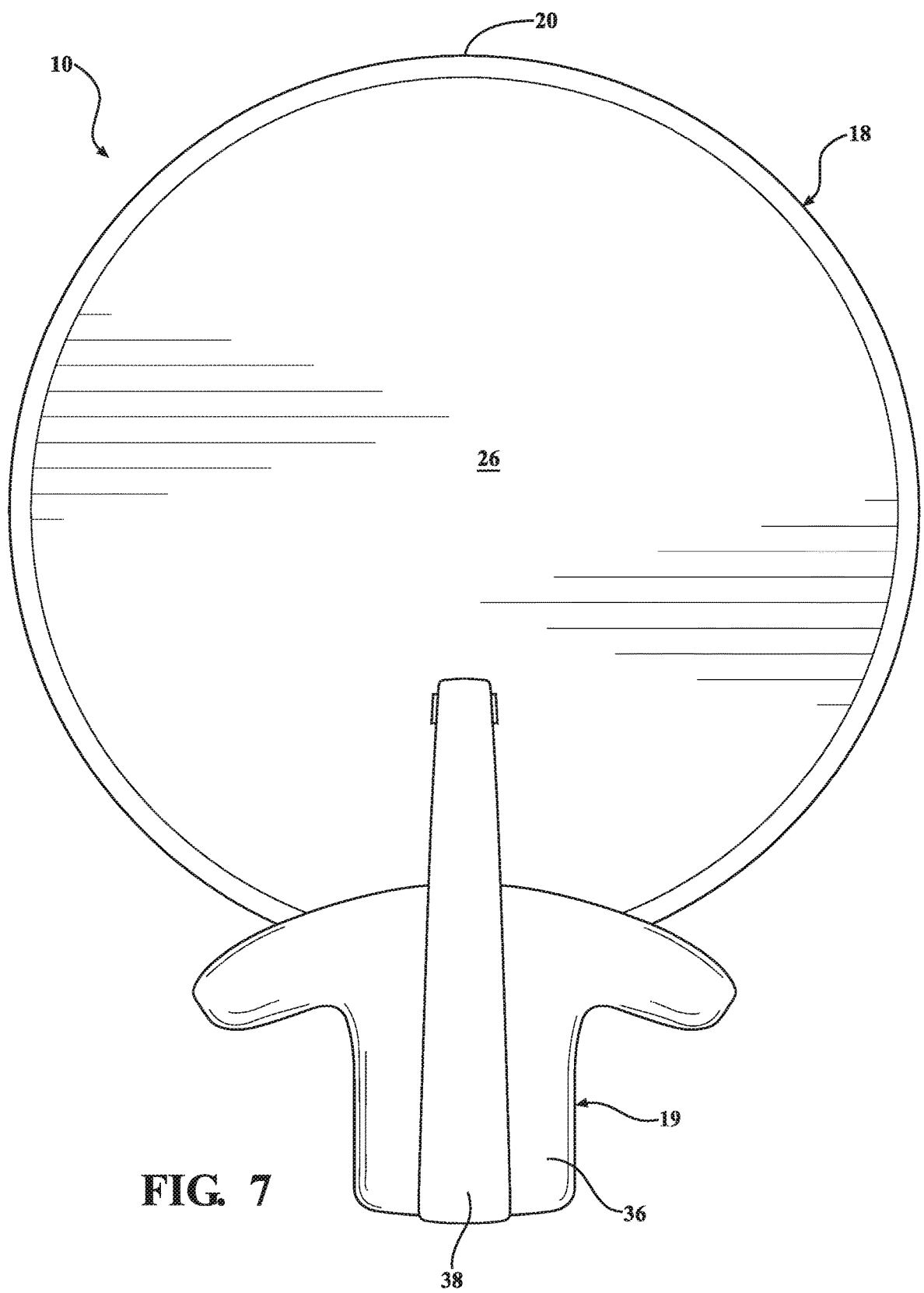
FIG. 7 is a plan view of the collapsible detection antenna of FIG. 1.

Referring to FIGS. 1 and 7, the support member 26 spans an interior chord or area of the antenna loop 20. In one embodiment, the support member 26 may span 10% to 100%, 25% to 100%, 50% to 100%, or 100% of an interior area of the antenna loop 20, the support member 26 may form various patterns across the interior area. For example, the support member 26 may comprise a series of parallel strands disconnected from one another.

Figure 6:
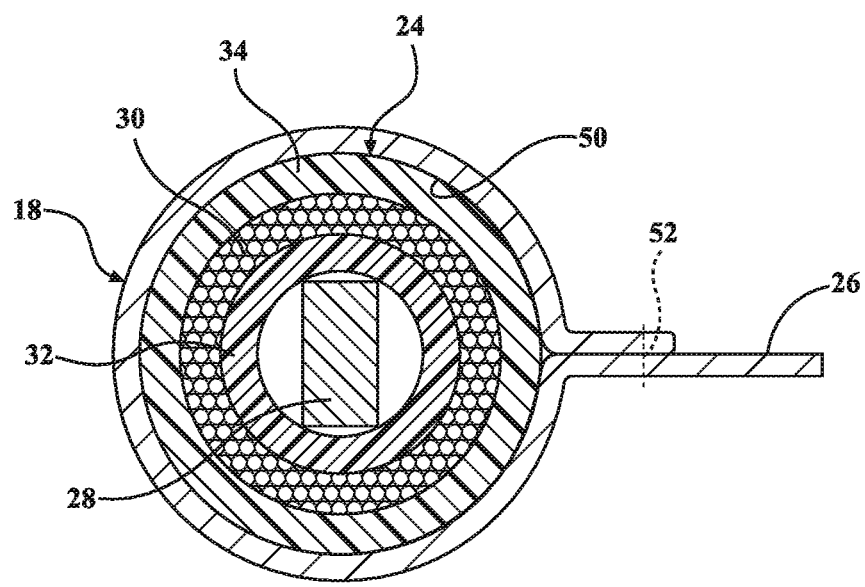
FIG. 6 is a cross-sectional view of one embodiment of the antenna assembly of the collapsible detection antenna of FIG. 1.

In one embodiment illustrated in FIG. 6, the support member 26 is attached to itself about a circumference to provide a channel 50 for the loop assembly 24 to pass through. In one embodiment, the support member 26 is sewn by at least one stitch 52 on itself along the circumference so to provide the channel 50 for the loop assembly 24 to pass through. In other embodiments, the support member 26 could be assembled by RF or ultrasonic-welding or with adhesive, i.e., the support member 26 may be bonded to itself such that the antenna assembly 18 is at least partially surrounded by the support member 26, or the support member 26 may be welded or adhered directly to the antenna assembly 18.

In various embodiments, the support member 26 may be transparent or translucent depending on the application. It should be appreciated that the support member 26 provides the radial support needed to maintain the shape of the loop assembly 24 when it is in the deployed configuration. It should also be appreciated that maintaining a repeatable shape is useful in certain embodiments for keeping the collapsible detection antenna 10 tuned during use so that the antenna assembly 18 can achieve its intended read range.

The collapsible detection antenna 10 may include a retaining member 54 to retain the antenna assembly 18 in the collapsed configuration. In one embodiment illustrated in FIGS. 11 and 20, the retaining member 54 may be an enclosure to allow the antenna assembly 18 to be disposed therein to collapse the antenna assembly 18. In another embodiment illustrated in FIGS. 21-26, the retaining member 54 may be one or more magnets. In yet another embodiment illustrated in FIGS. 27-28, the retaining member 54 may be a hook material or a loop material. In still another embodiment illustrated in FIGS. 29 and 30, the retaining member 54 may be one or more strings. In a further embodiment illustrated in FIGS. 31 and 32, the retaining member 54 may be one or more a zippers. It should be appreciated that the retaining member 54 is optional. It should also be appreciated that, in most embodiments, the collapsible detection antenna 10 is stable in the collapsed position and the deployed position and does not require a means of retaining or containment.

Figure 31:
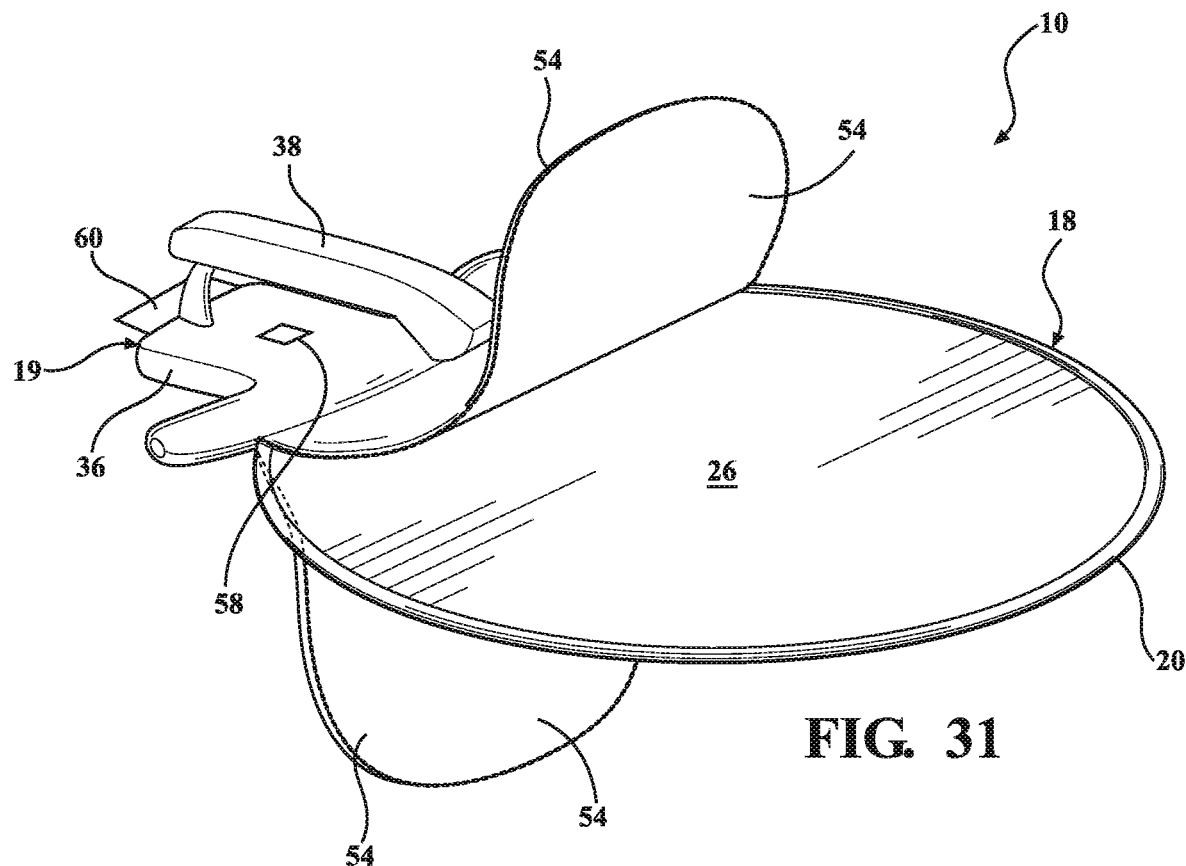
FIG. 31 is a perspective view of a still further embodiment of a method, according to the present invention, of collapsing the collapsible detection antenna of FIG. 1 illustrating a first step of collapsing the collapsible detection antenna.
Figure 32:
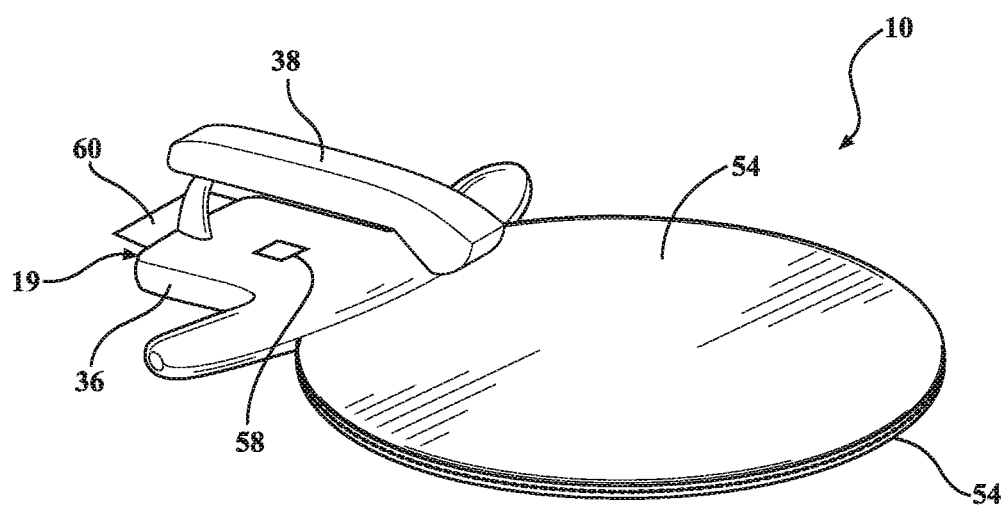
FIG. 32 is a view similar to FIG. 31 illustrating a second step of collapsing the collapsible detection antenna.

Referring to FIGS. 31 and 32, the collapsible detection antenna 10 may include an emitter 58 coupled to the housing 36 to emit an audible tone or visual tone upon detection of the electromagnetic tags 12. In another embodiment, the collapsible detection antenna 10 may include a feedback module 60 coupled to the housing 19 to provide haptic feedback upon detection of the electromagnetic tags 12. During the intended use of the collapsible detection antenna 10, the user requires ample feedback to be notified of a change in the status of the antenna 10 to the presence of a surgical article 14 present in the field such as the operating room 16. In one embodiment for the emitter 58, improved visual feedback can be achieved by placing one or more light emitting diodes (LEDs) 62 (FIGS. 35-41) in the housing 19 of the antenna 10 and attaching a flexible light pipe (not shown) to an outside perimeter of the antenna loop 20. This will illuminate the perimeter of the antenna loop 20 when the electromagnetic tag 12 is detected or if the antenna loop 20 is not in its correct shape, thus providing a much clearer indication to the user.

In other embodiments, the support member 26 may be used as a screen to project status icons and/or object detection feedback. This can be done by placing the LEDs 62 in the base 36 or handle 38 of the housing 19 and pointing onto the reflective surface created by the support member 26. In some embodiments, this is accomplished by use of miniature Pico projector (not shown), which can project additional information such as instructions for use, serial number, and description of the surgical article 14 missing and description of the surgical article 14 found. Further in addition to visual and audio, the emitter 58 may provide haptic feedback that may be used to vibrate the handle 38 of the housing 19 as an indictor to alert the user that the electromagnetic tag 12 was detected in the field of the operating room 16 or if the user is improperly using the collapsible detection antenna 10. It should be appreciated that one such example of this may be if the user is scanning with the collapsible detection antenna 10 by moving too quickly at rate that would not produce reliable results. It should also be appreciated that these embodiments may be used independently or in any combination of the above features.

Figure 36:
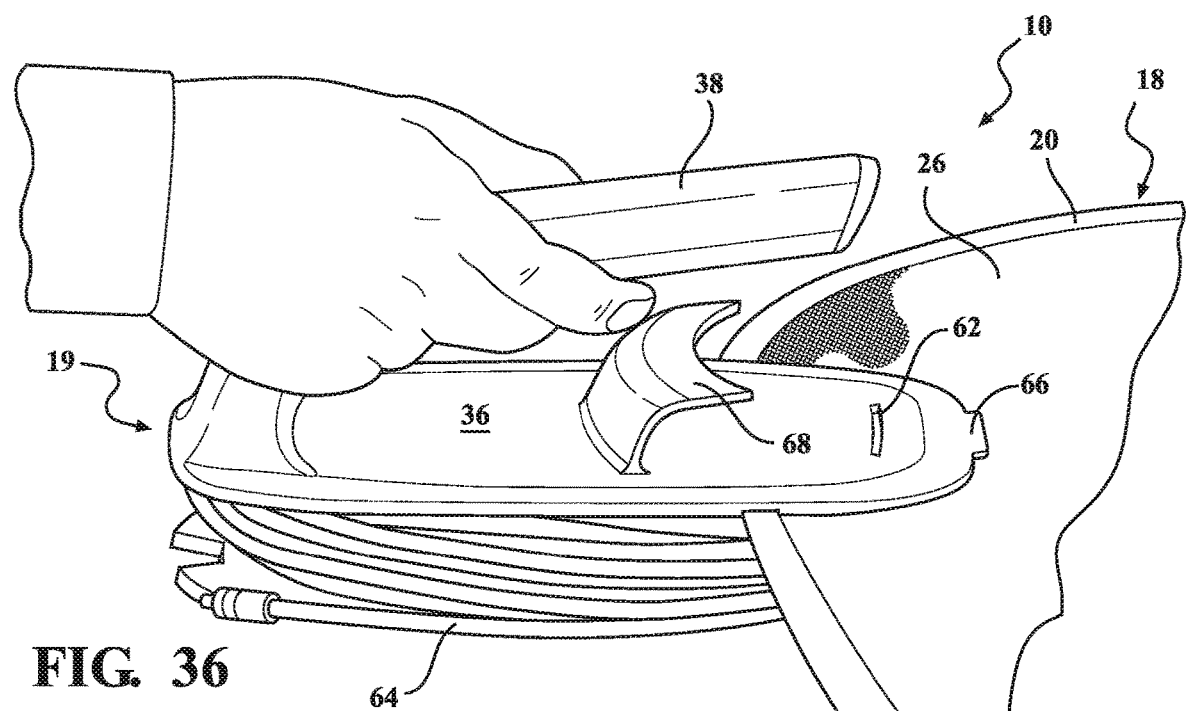
FIG. 36 is a perspective view of the embodiment as in FIG. 35 in an initial configuration.
Figure 37:
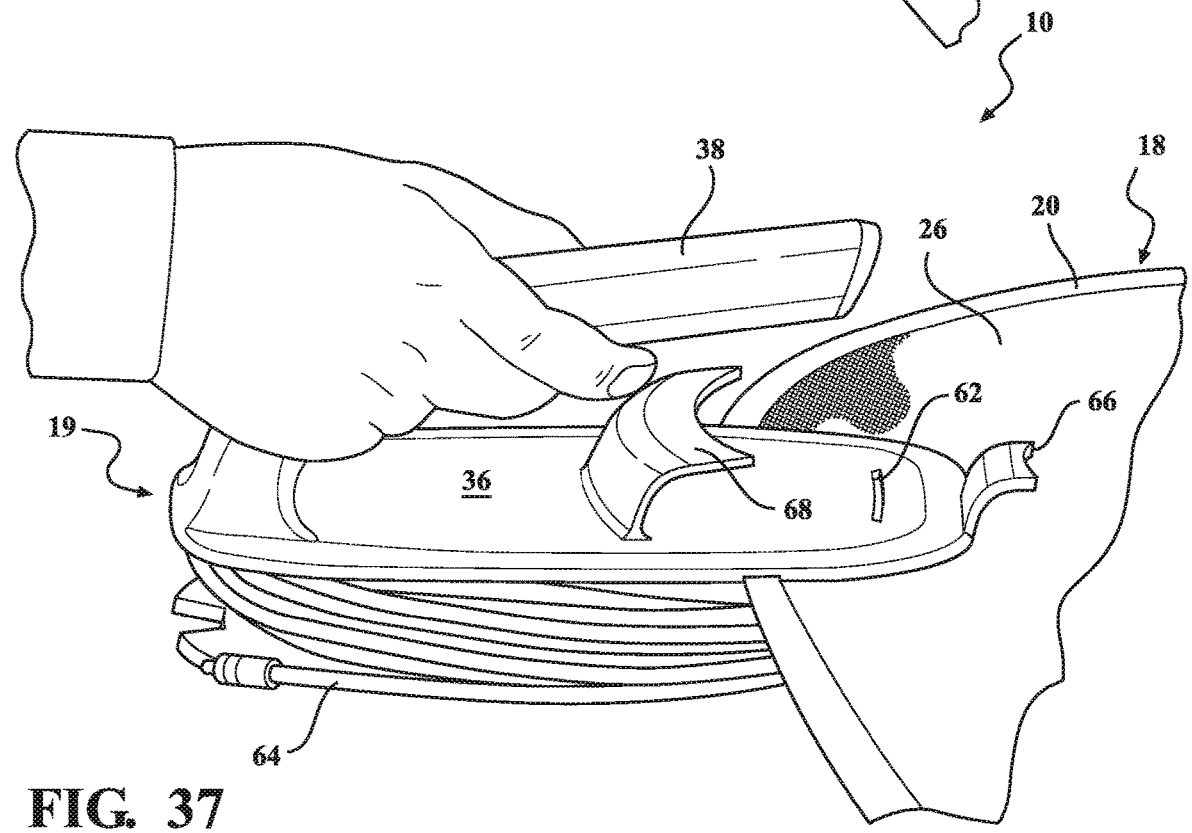
FIGS. 37-45 illustrate yet still a further embodiment, according to the present invention, of the collapsible detection antenna of FIG. 1 illustrating a series of steps of collapsing the collapsible detection antenna.

In another embodiment illustrated in FIGS. 36 and 37, the wire 22 may be in the form of a cord or cable 64 and wrapped about the base 36 of the housing 19. It should be appreciated that the cable 64 is located below the antenna assembly 18 and relative to the housing 19.

In yet another embodiment illustrated in FIGS. 35-45, the collapsible detection antenna 10 may include a front or forward tab 66 coupled to the base 36 of the housing 19 to assist in holding the antenna assembly 18 during collapsing. The collapsible detection antenna 10 may also include a retaining or holding member 68 coupled to the base 36 of the housing 19 to retain or hold the antenna assembly 18 in the collapsed configuration. In FIGS. 35-36, the forward tab 66 is a flat extension from the base 36 of the housing 19. In FIGS. 37-44, the forward tab 66 is a curved extension from the base 36 of the housing 19 that may aid the user in locating the antenna assembly 18 during collapsing. In further alternative embodiments, the tab 66 may be an alternative form suitable to assist in collapsing the antenna assembly 18. In the embodiments illustrated, the holding member 68 has a generally inverted "L" shape. In this embodiment, the tab 66 and member 68 are integral, unitary, and formed as one-piece with the base 36 of the housing 19. In alternative embodiments, the tab 66 and the member 68 may be coupled to the housing 19 using suitable means, including mechanical fastening means, adhesives or the like.

Referring to FIGS. 7-11, the present invention provides a method, according to one embodiment of the present invention, of collapsing a collapsible detection antenna 10 used to detect electromagnetic tags 12 of surgical articles 14. The method includes the steps of providing an antenna assembly 18 configured to detect the electromagnetic tags 12. The antenna assembly 18 is configured to move between a deployed configuration and a collapsed configuration. In the deployed configuration, the antenna assembly 18 forms an antenna loop 20 configured to detect the electromagnetic tags 12. The antenna assembly 18 has a greater detection range in the deployed configuration than in the collapsed configuration. The deployed configuration corresponds to a tuned shape of the antenna assembly 18 sufficient to detect the electromagnetic tags 12 in the deployed configuration. The method also includes the steps of collapsing the antenna assembly 18 from the deployed configuration to the collapsed configuration. In another embodiment, the method may include the steps of retaining the antenna assembly 18 in the collapsed configuration. It should be appreciated that the antenna assembly 18 can take many different shapes in its collapsed configuration.

Figure 8:
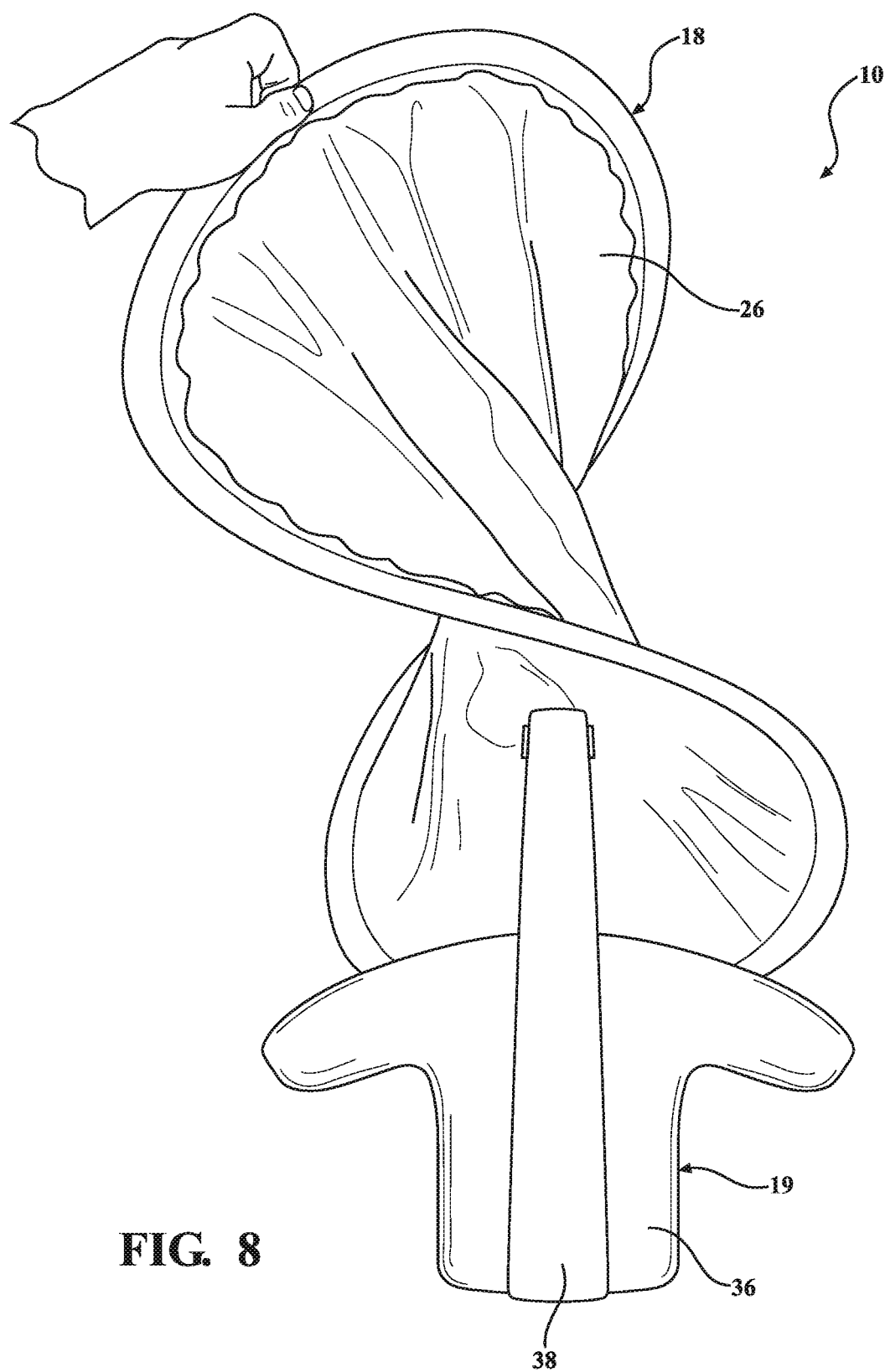
FIG. 8 is a view of one embodiment of a method, according to the present invention, of collapsing the collapsible detection antenna of FIG. 1 illustrating a first step of collapsing the collapsible detection antenna.
Figure 9:
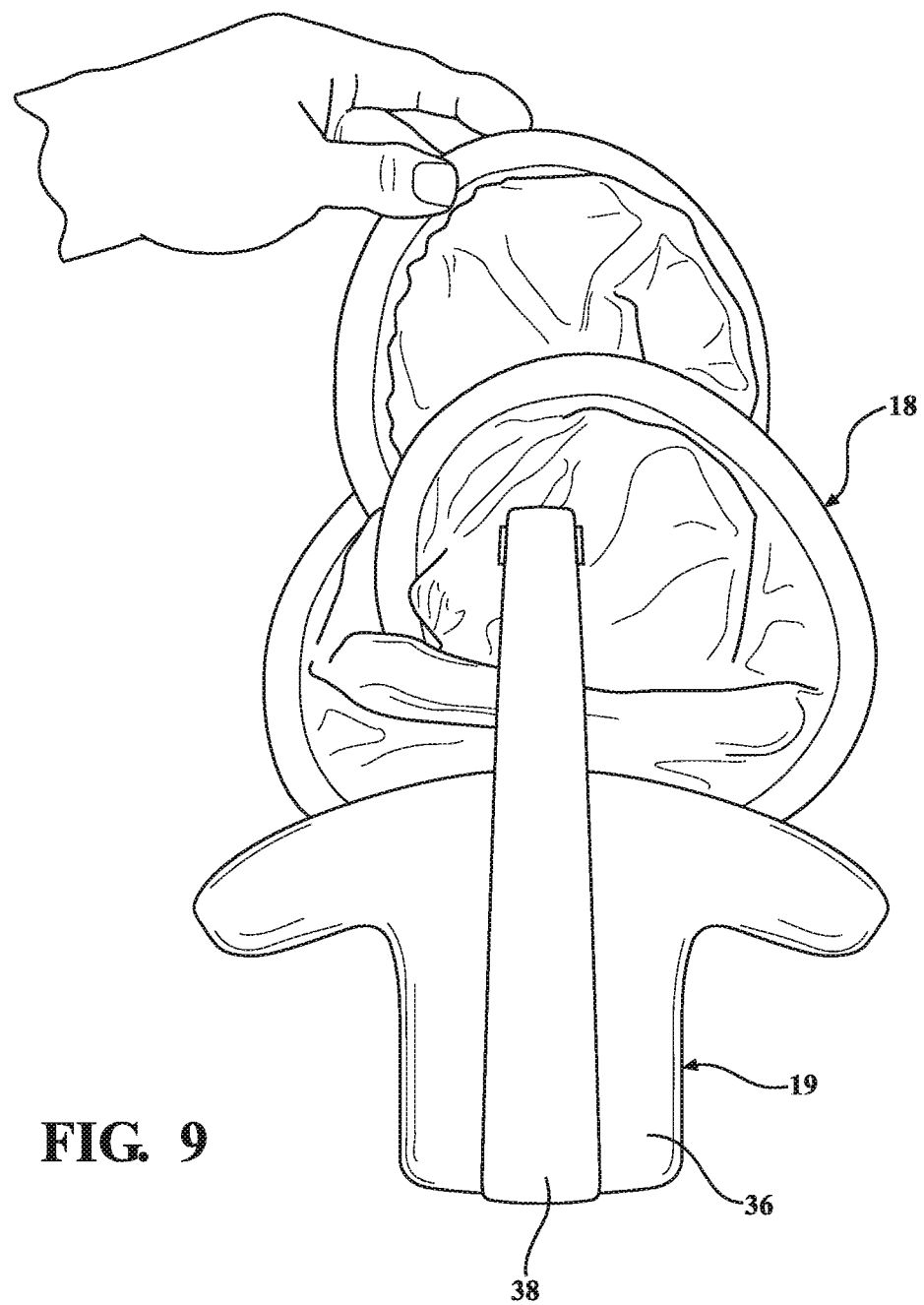
FIG. 9 is a view similar to FIG. 8 illustrating a second step of collapsing the collapsible detection antenna.
Figure 10:
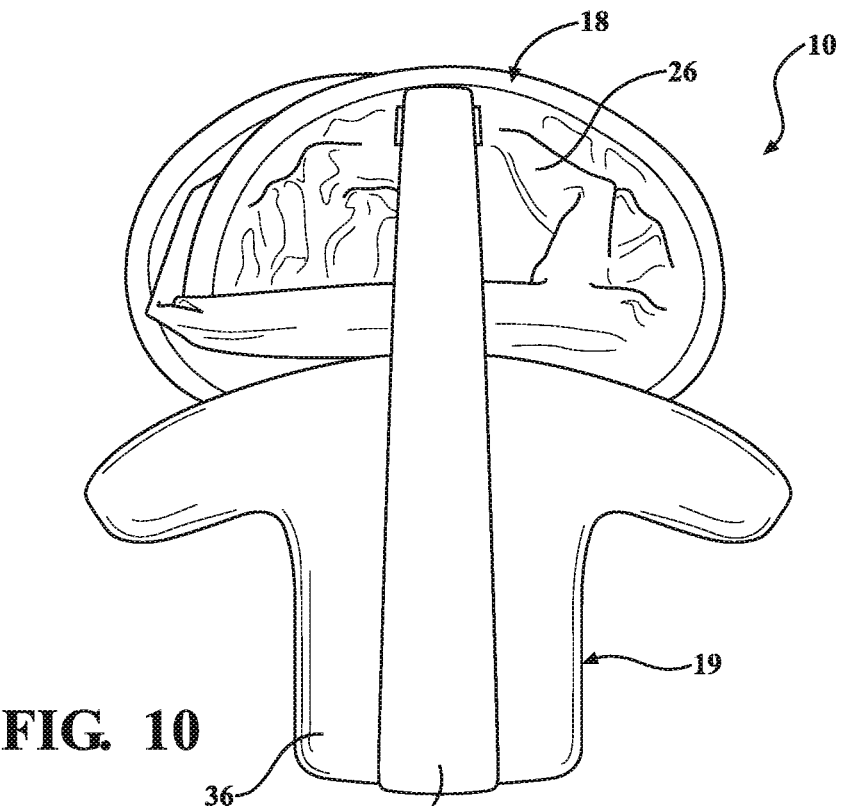
FIG. 10 is a view similar to FIG. 8 illustrating a third step of collapsing the collapsible detection antenna.
Figure 11:
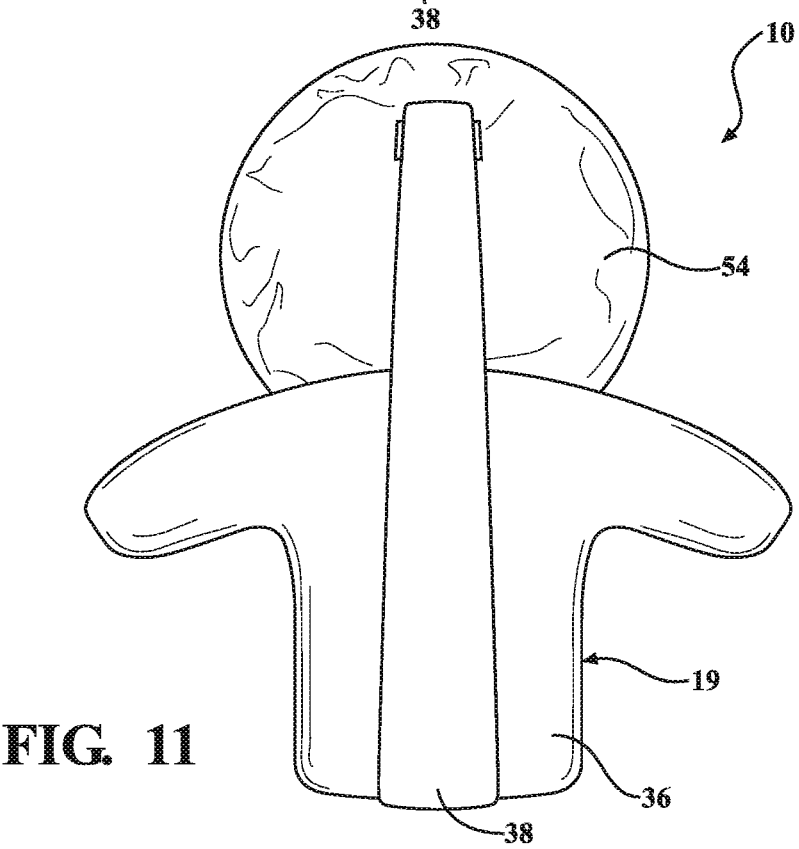
FIG. 11 is a view similar to FIG. 8 illustrating a fourth step of collapsing the collapsible detection antenna.
Figure 12:
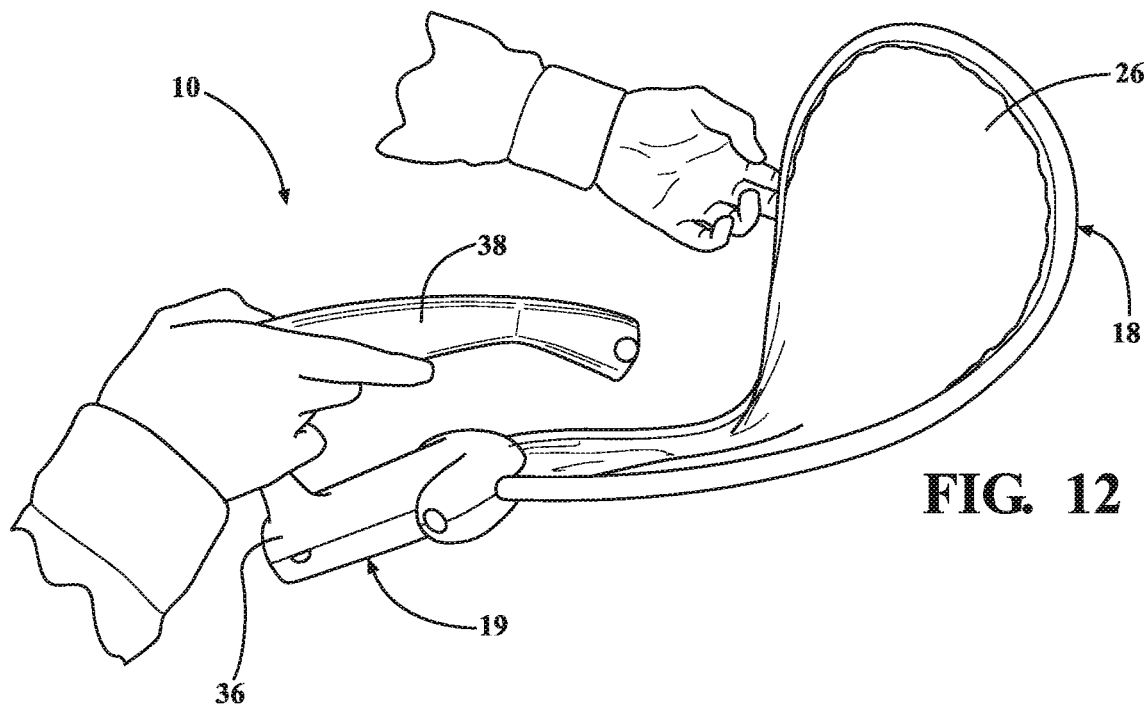
FIG. 12 is a view of another embodiment of a method, according to the present invention, of collapsing the collapsible detection antenna of FIG. 1 illustrating a first step of collapsing the collapsible detection antenna.

In the embodiment illustrated in FIGS. 7-11, the step of collapsing may be using a twisting motion to collapse the antenna assembly 18. As illustrated in FIG. 7, the antenna assembly 18 is in the deployed configuration. As illustrated in FIG. 8, the method also includes the steps of using a twisting motion such as by the user grasping a distal end of the antenna assembly 18 with the hand of the user and twisting the antenna assembly 18. As illustrated in FIG. 9, the method includes the step of using a 360 degree twisting motion by the user to collapse the antenna assembly 18. As illustrated in FIG. 10, the method includes the step of collapsing the antenna assembly 18 from the deployed configuration to the collapsed configuration. In the collapsed configuration, the diameter of the antenna assembly 18 is approximately 2-4 times less than the diameter of the antenna assembly 18 in the deployed configuration and approximately 2-10 times smaller in surface area than the antenna assembly 18 in the deployed configuration. As illustrated in FIG. 11, the method may include the step of retaining the antenna assembly 18 in the collapsed configuration.

Figure 13:
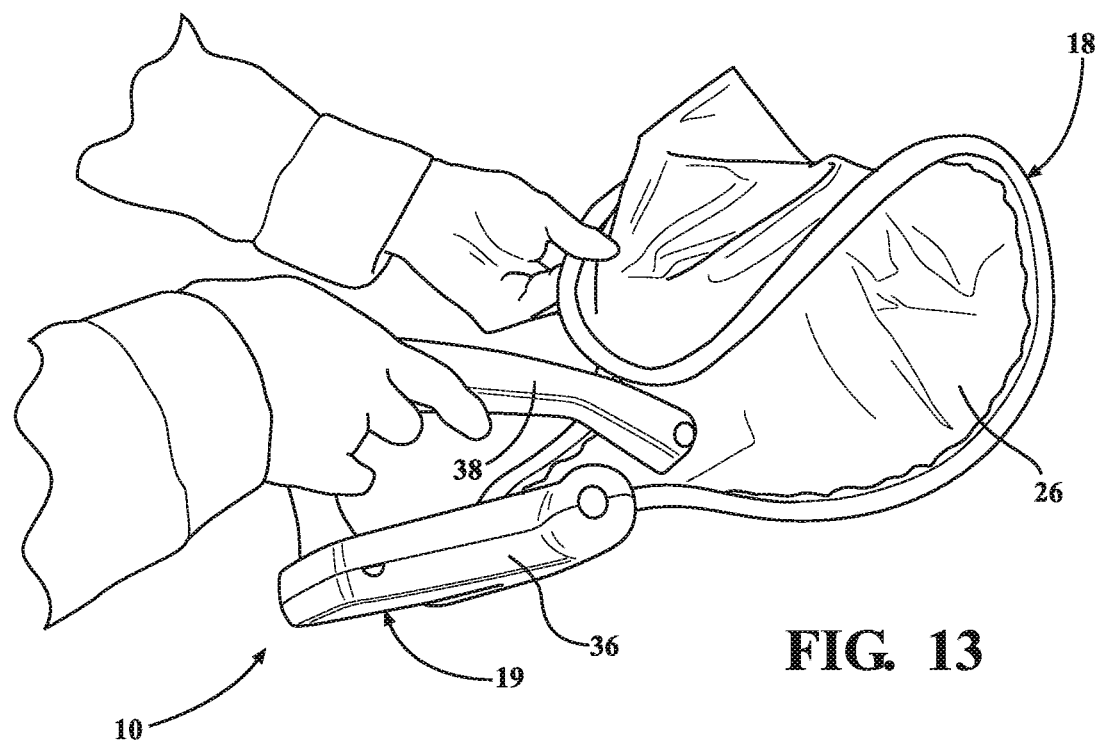
FIG. 13 is a view similar to FIG. 12 illustrating a second step of collapsing the collapsible detection antenna.
Figure 14:
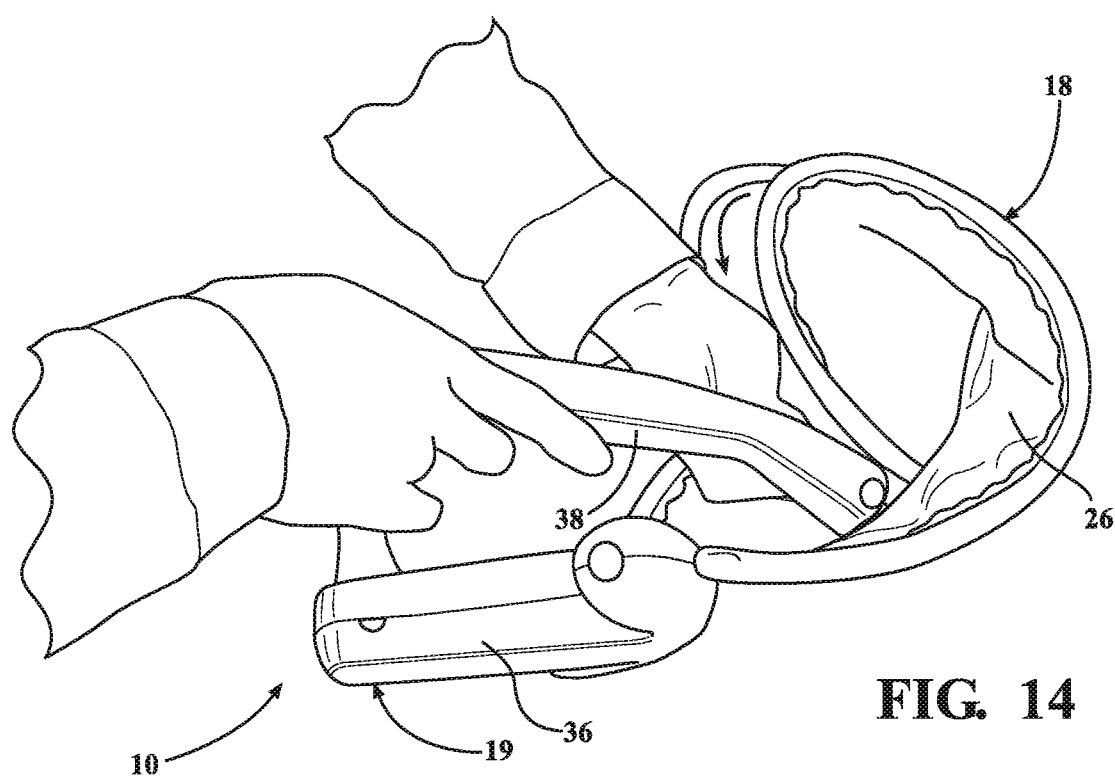
FIG. 14 is a view similar to FIG. 12 illustrating a third step of collapsing the collapsible detection antenna.
Figure 15:
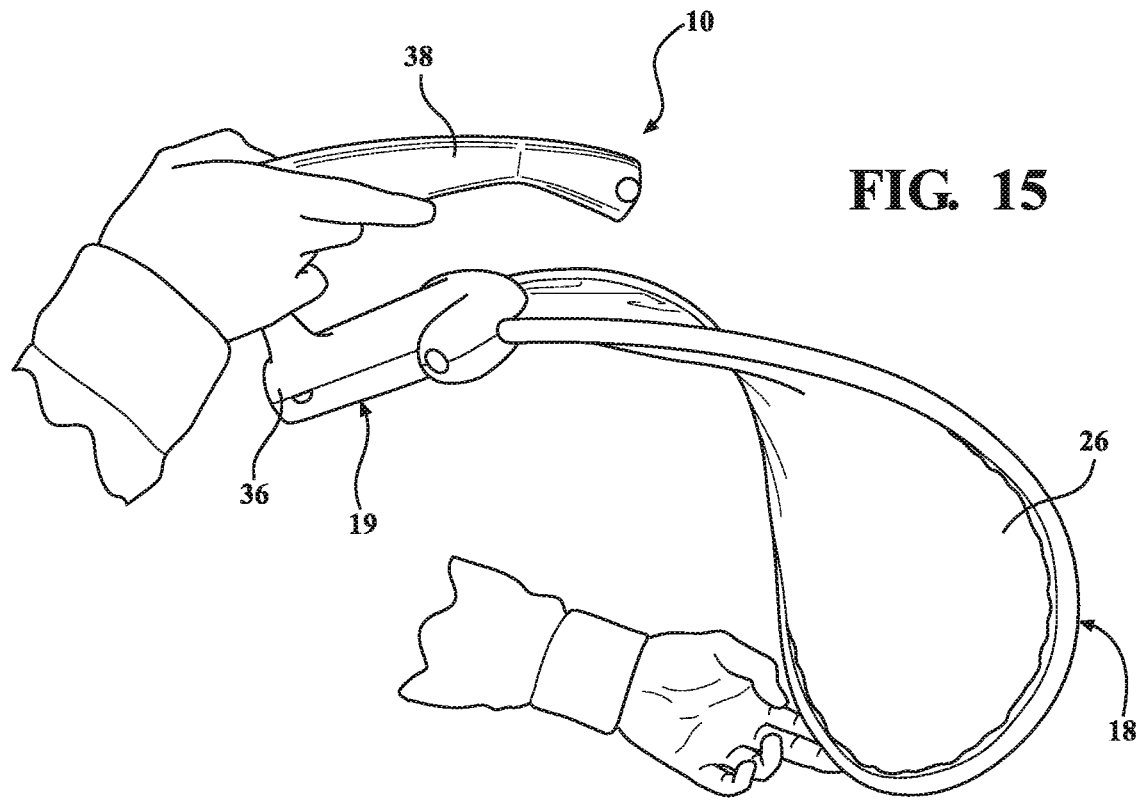
FIG. 15 is a view of yet another embodiment of a method, according to the present invention, of collapsing the collapsible detection antenna of FIG. 1 illustrating a first step of collapsing the collapsible detection antenna.
Figure 19:
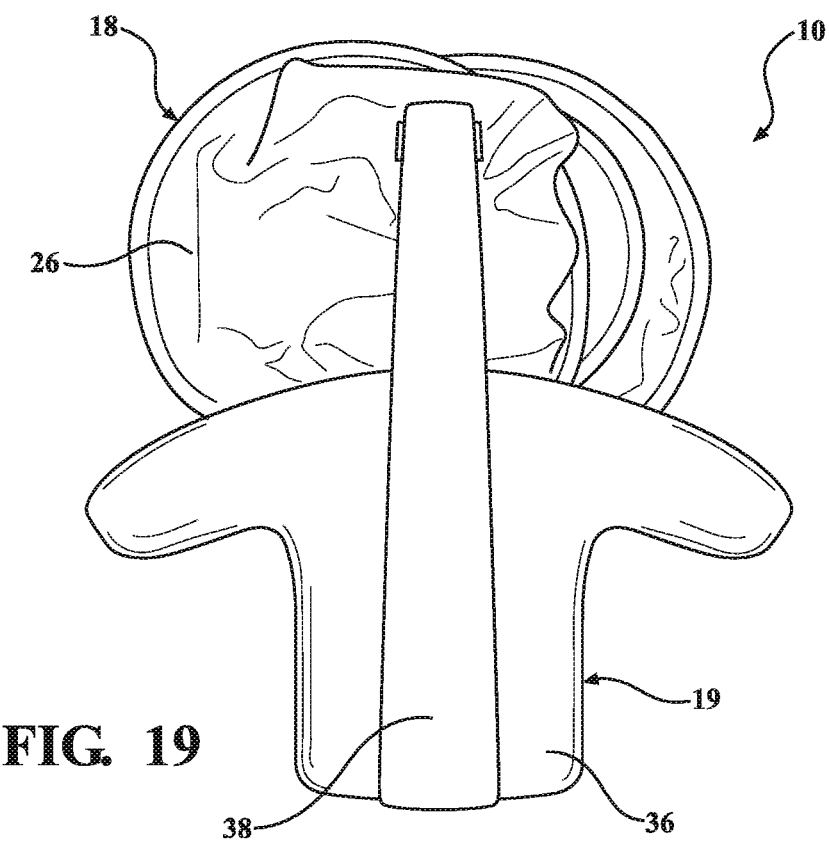
FIG. 19 is a view similar to FIG. 18 illustrating a fifth step of collapsing the collapsible detection antenna of FIGS. 12 and 15.
Figure 20:
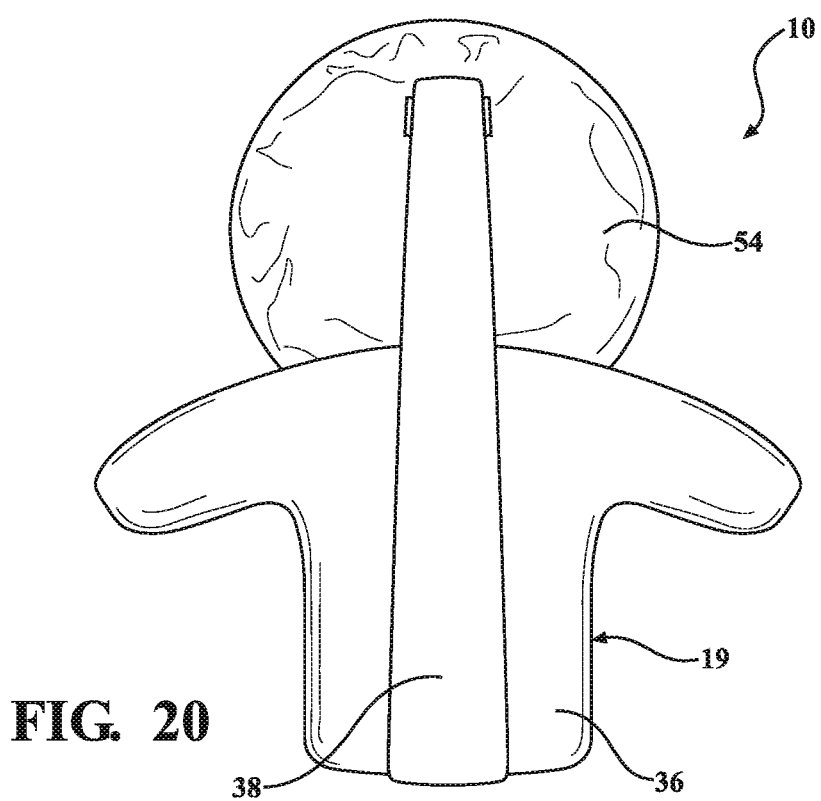
FIG. 20 is a view similar to FIG. 18 illustrating a sixth step of collapsing the collapsible detection antenna of FIGS. 12 and 15.

In another embodiment illustrated in FIGS. 12-14 and 18-20, the step of collapsing may be grasping the antenna assembly 18 with a hand of the user at a distal end from the housing 19. As illustrated in FIG. 13, the method includes the step of pulling the antenna assembly 18 upward toward the handle 38 to collapse the antenna assembly 18. As illustrated in FIG. 14, the method includes the step of folding the antenna assembly 18 back on itself. As illustrated in FIGS. 18 and 19, the method includes the step of collapsing the antenna assembly 18 to a much more compact size approximately 3 times smaller in diameter and 9 times smaller in surface area. As illustrated in FIG. 20 the method may include the step of retaining the antenna assembly 18 in the collapsed configuration.

Figure 16:
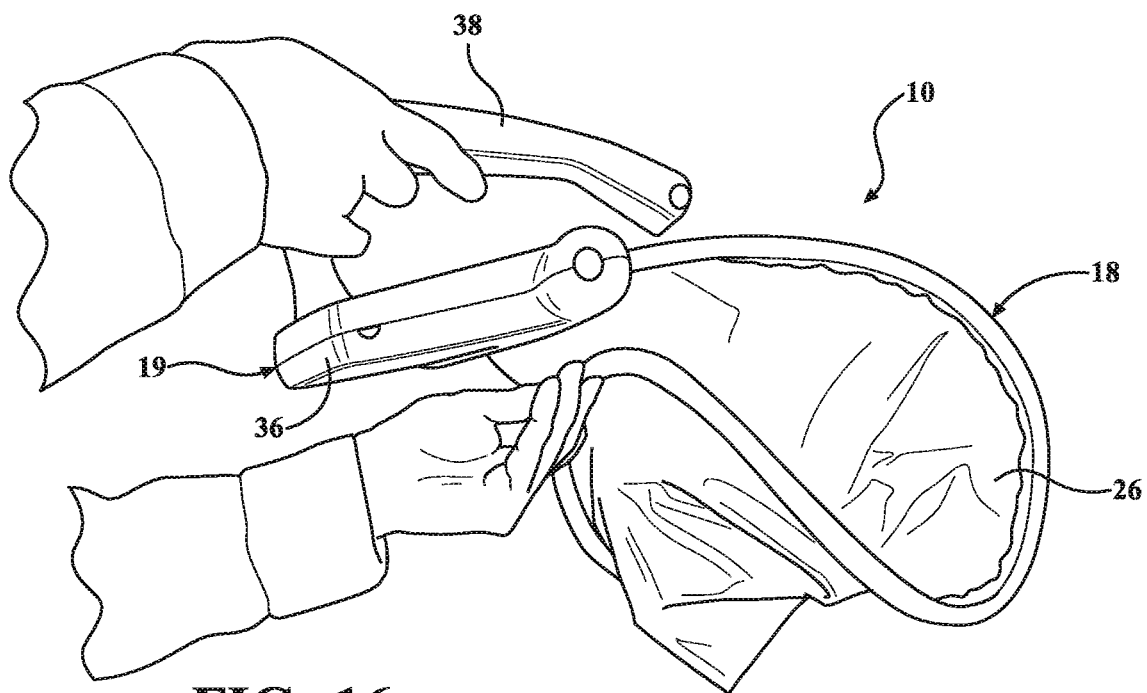
FIG. 16 is a view similar to FIG. 15 illustrating a second step of collapsing the collapsible detection antenna.
Figure 17:
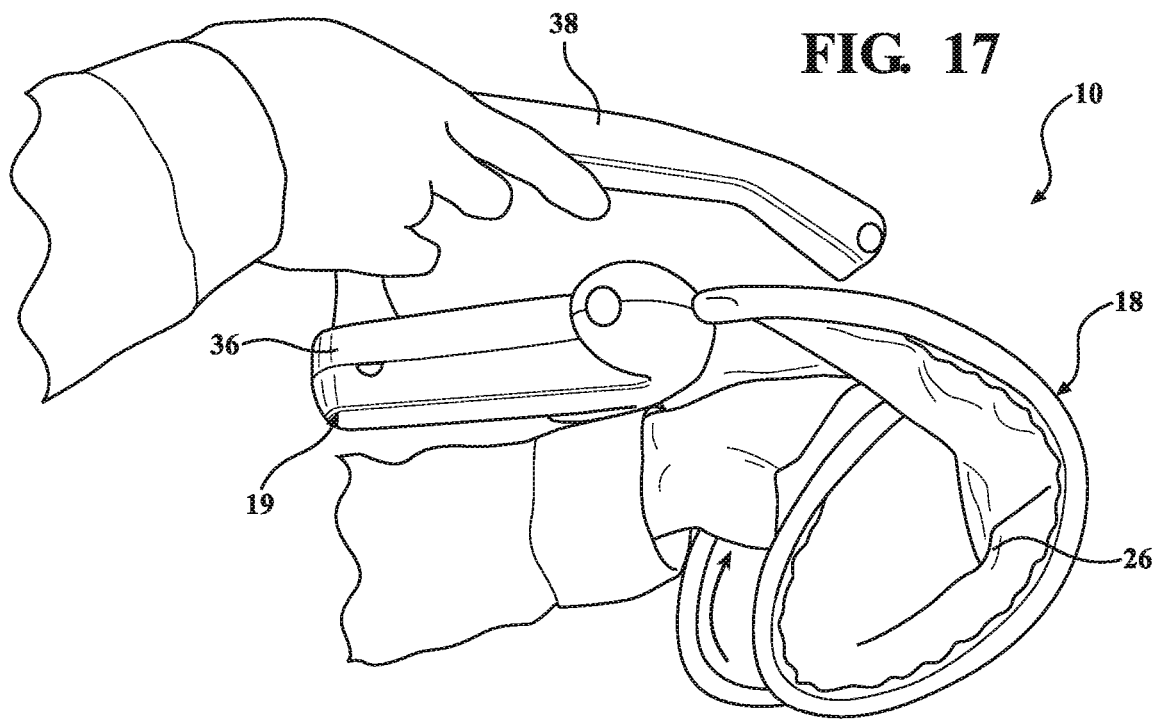
FIG. 17 is a view similar to FIG. 15 illustrating a third step of collapsing the collapsible detection antenna.

In yet another embodiment illustrated in FIGS. 15-20, the step of collapsing may be grasping the antenna assembly 18 with a hand of the user at a distal end from the housing 19. As illustrated in FIG. 16, the method includes the step of pulling the antenna assembly 18 downward toward the handle 38 to collapse the antenna assembly 18. As illustrated in FIG. 17, the method includes the step of folding the antenna assembly 18 back on itself. As illustrated in FIGS. 18 and 19, the method includes the step of collapsing the antenna assembly 18 to a much more compact size approximately 3 times smaller in diameter and 9 times smaller in surface area. As illustrated in FIG. 20, the method may include the step of retaining the antenna assembly 18 in the collapsed configuration.

Figure 21:
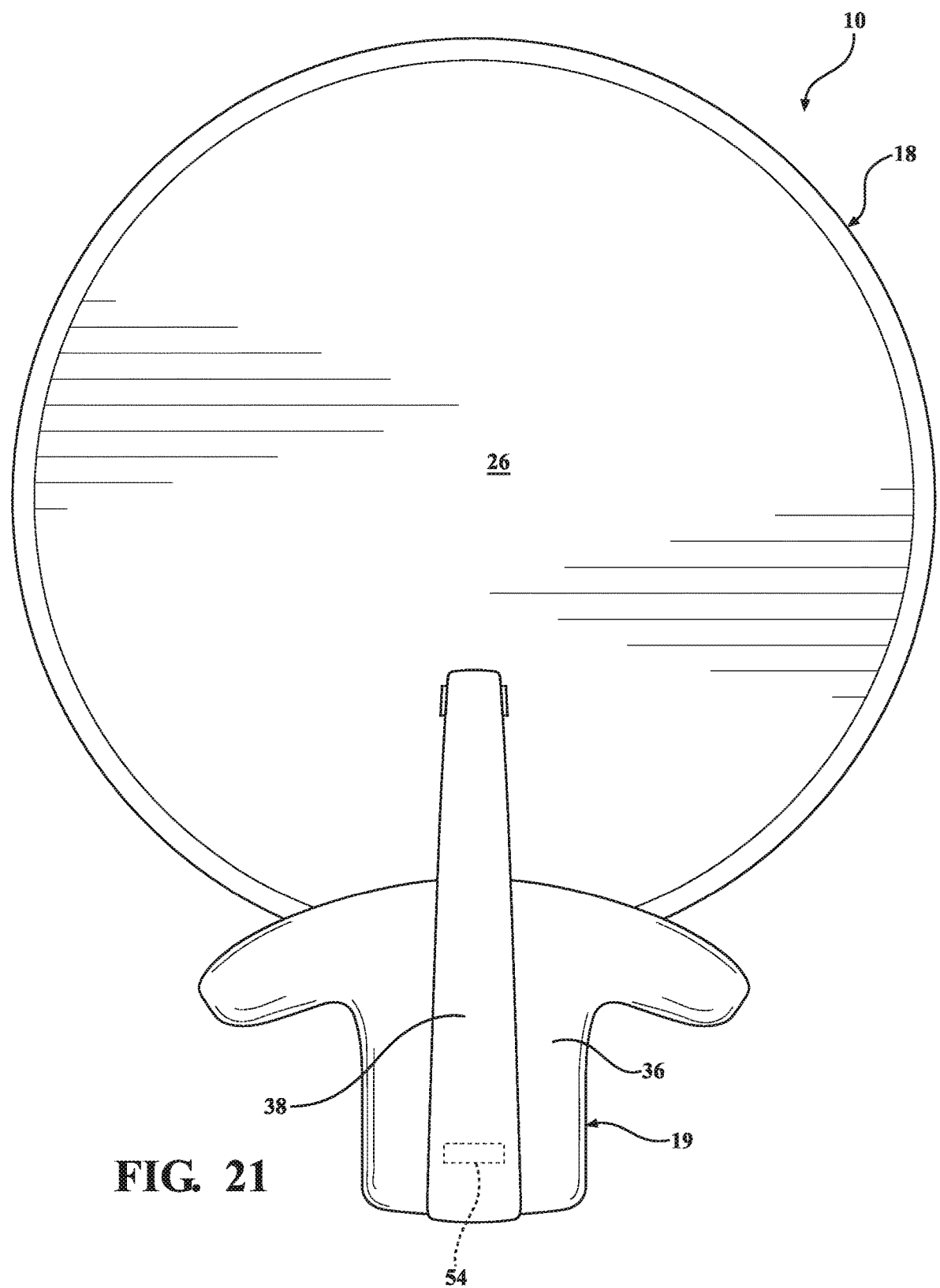
FIG. 21 is a view of yet another embodiment of a method, according to the present invention, of collapsing the collapsible detection antenna of FIG. 1 illustrating a first step of collapsing the collapsible detection antenna.
Figure 22:
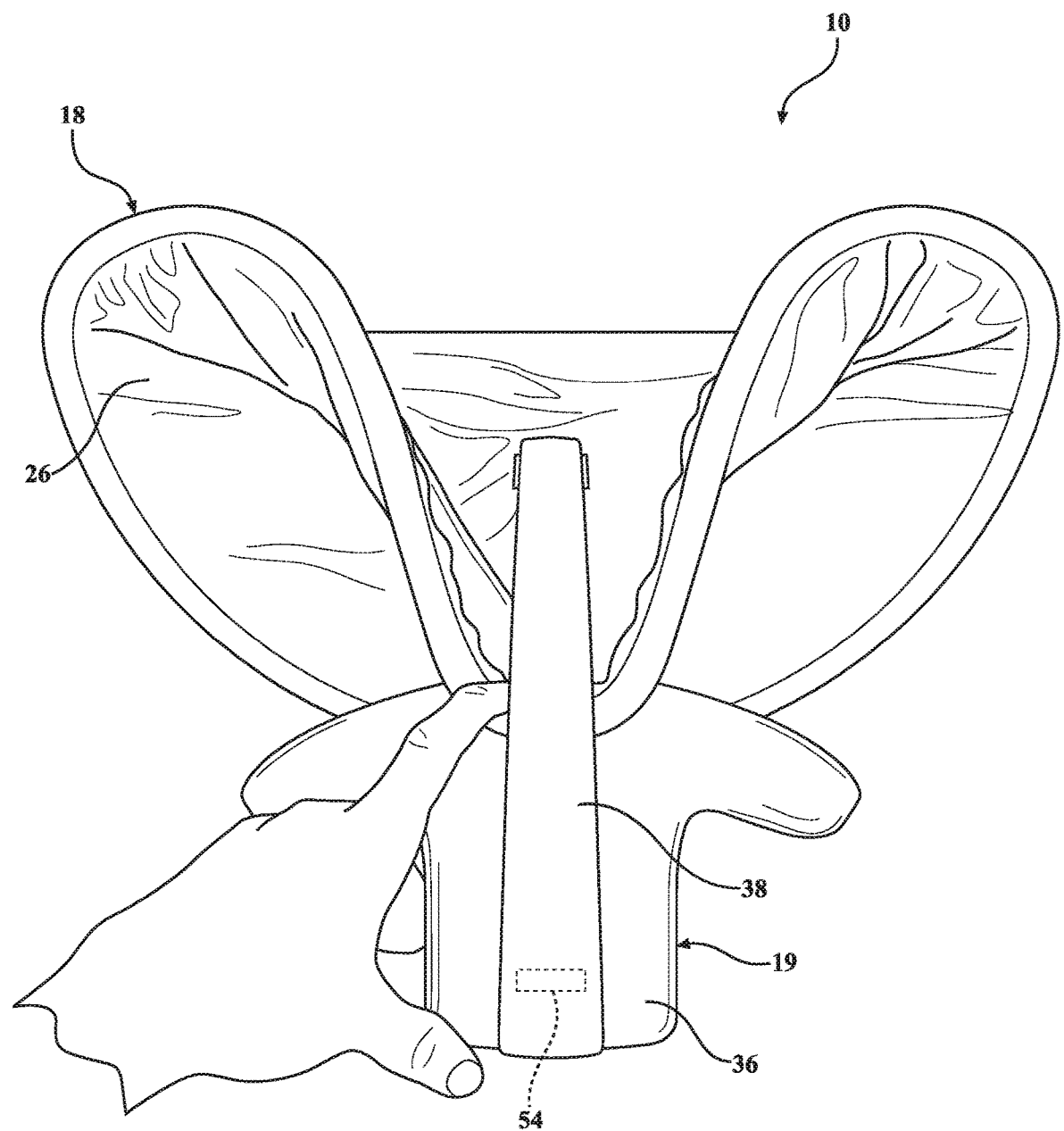
FIG. 22 is a view similar to FIG. 21 illustrating a second step of collapsing the collapsible detection antenna.
Figure 23:
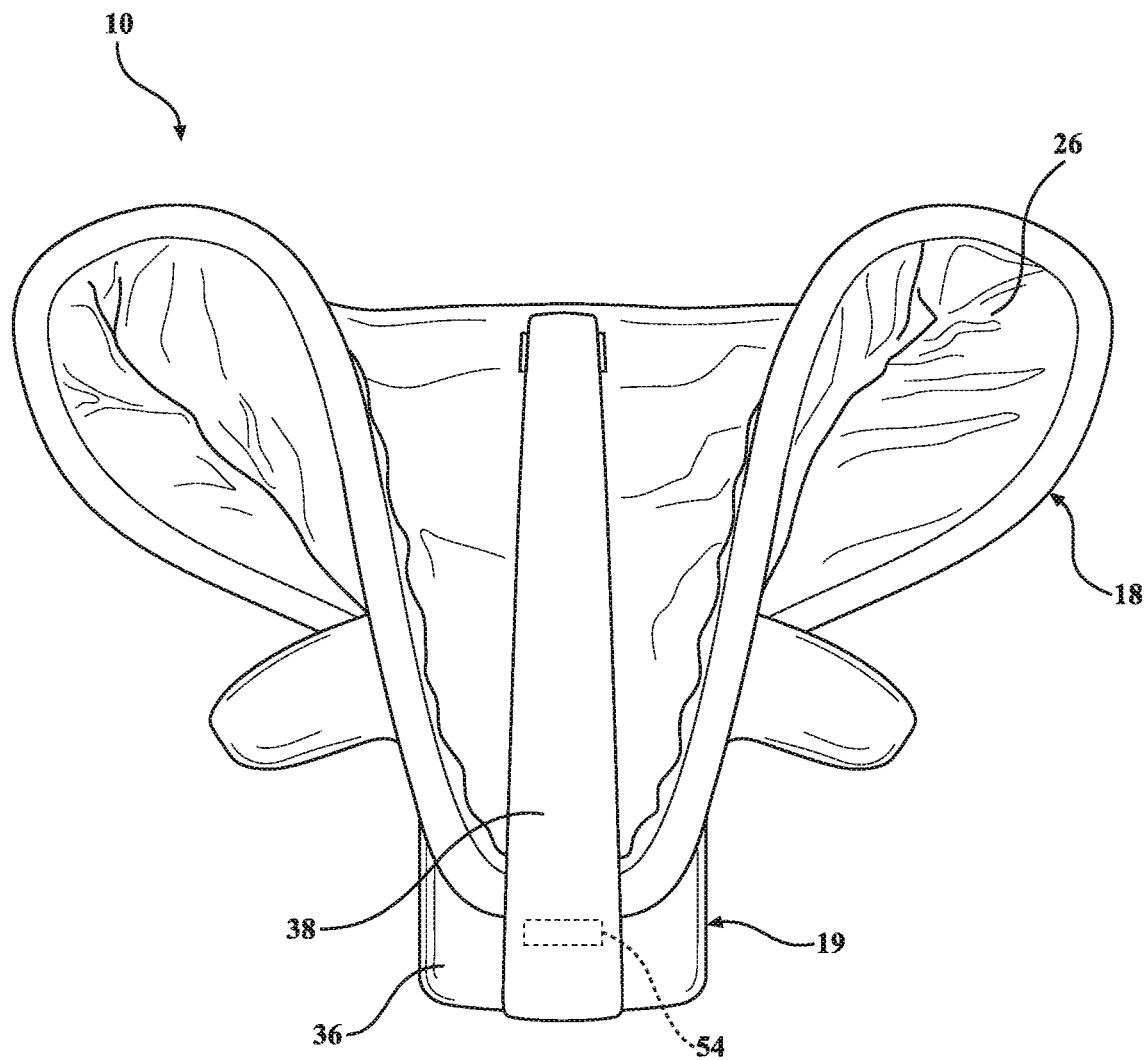
FIG. 23 is a view similar to FIG. 21 illustrating a third step of collapsing the collapsible detection antenna.
Figure 24:
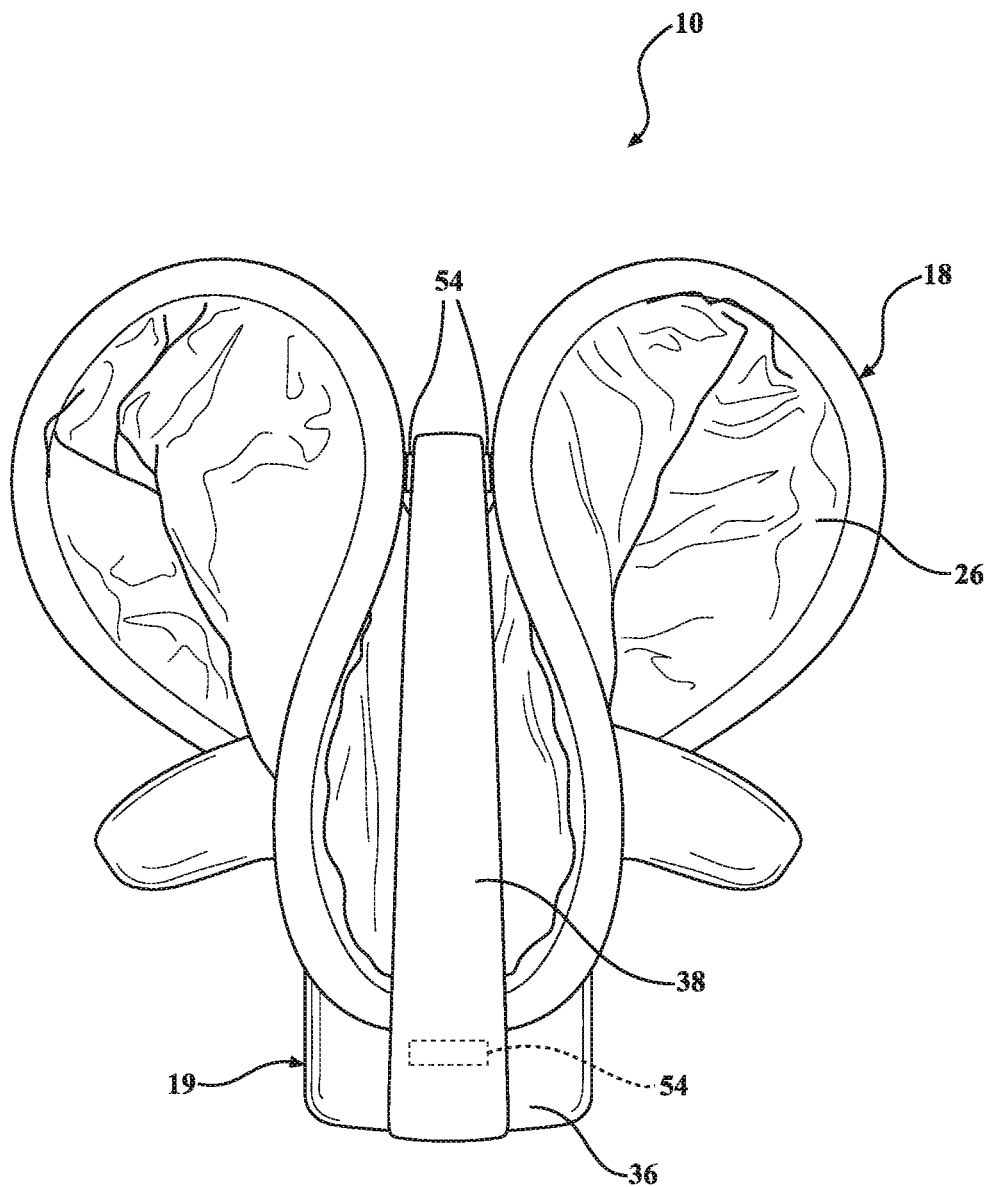
FIG. 24 is a view similar to FIG. 21 illustrating a fourth step of collapsing the collapsible detection antenna.

In yet another embodiment illustrated in FIGS. 21-24, the step of collapsing may be using the retaining member 54 in the form of a magnet coupled to the housing 19 to attract the antenna assembly 18 toward the housing 19 when the magnets are brought into proximity. As illustrated in FIG. 21, the antenna assembly 18 is in the deployed configuration. As illustrated in FIG. 22, the method includes the step of grasping the antenna assembly 18 by the hand of the user at the front or distal edge (away from the handle 38) and pulling the antenna assembly 18 toward the handle 38. As illustrated in FIG. 23, the method may include the step of retaining the antenna assembly 18 with the retaining member 54. As illustrated in FIG. 24, the method may include the step of retaining the antenna assembly 18 in the collapsed configuration. In this embodiment, the retaining member 54 is a magnet built into the handle 38 of the housing 19 that holds the antenna loop 20 of the antenna assembly 18 in place. In this embodiment, the steel used in the spring steel of the structural member 28 is ferrite-based so that the magnetic retaining member 54 would attract the structural member 28 as soon as the antenna assembly 18 is brought close to or in contact with the handle 38.

Figure 25:
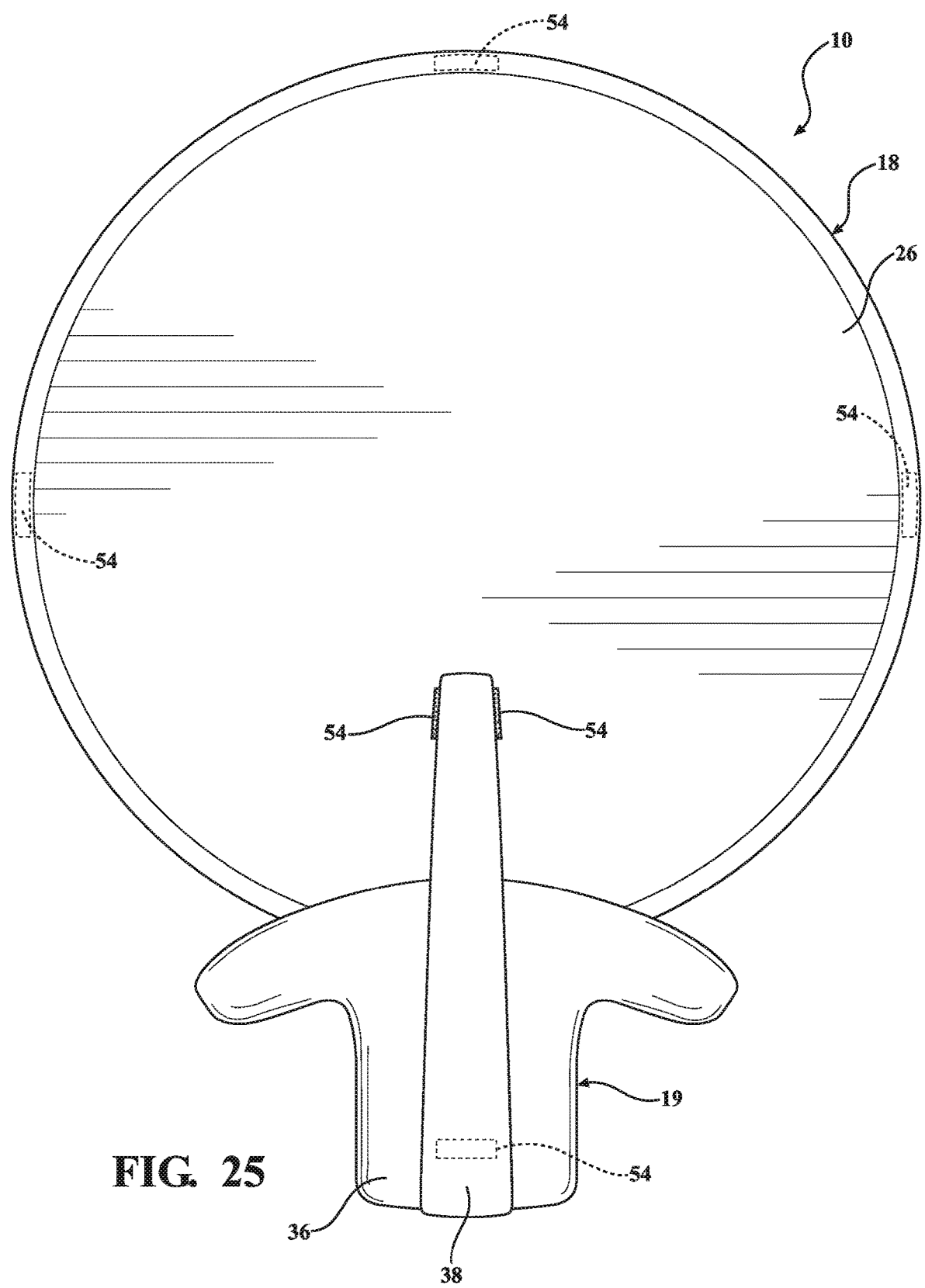
FIG. 25 is a view of still another embodiment of a method, according to the present invention, of collapsing the collapsible detection antenna of FIG. 1 illustrating a first step of collapsing the collapsible detection antenna.
Figure 26:
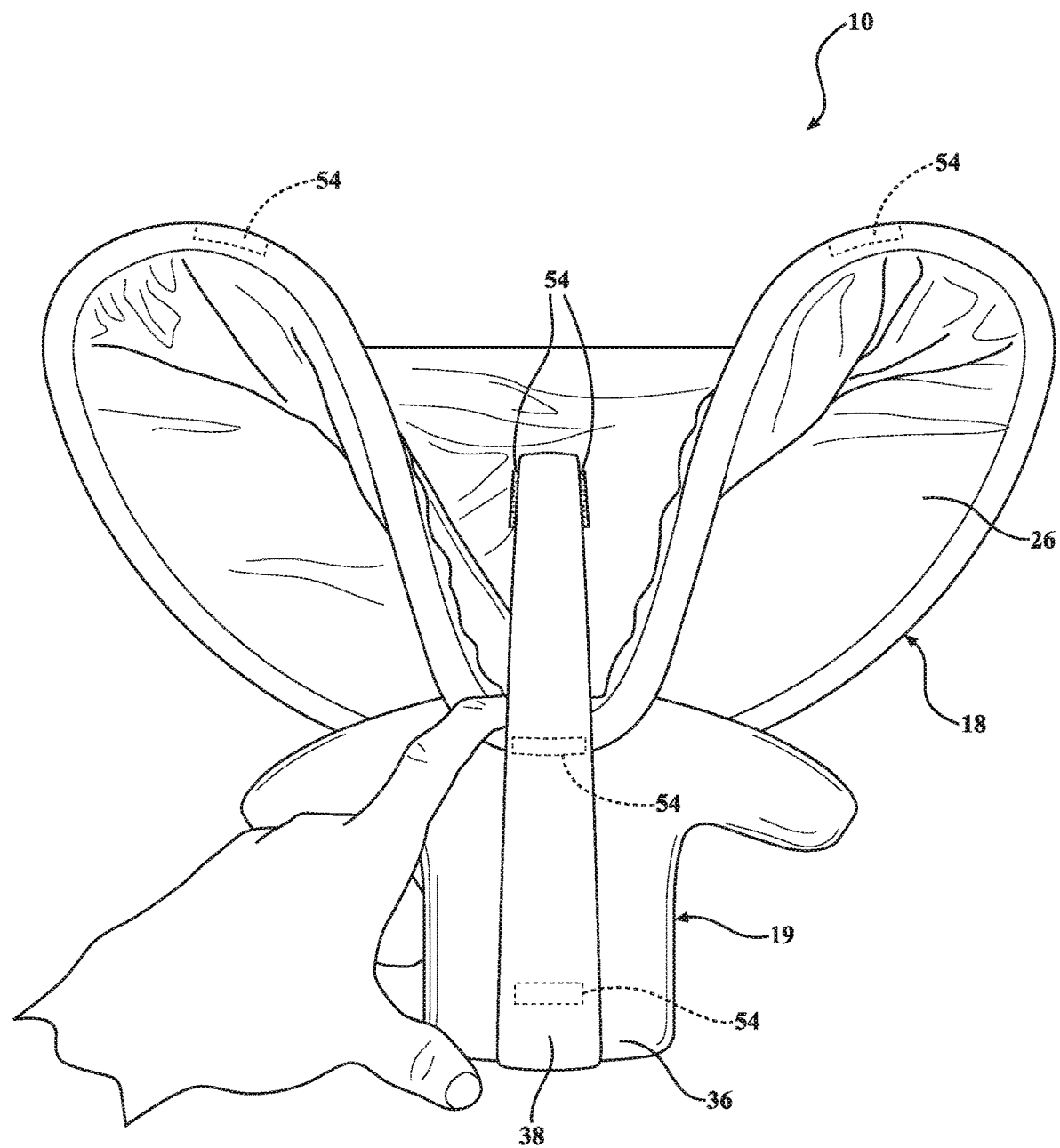
FIG. 26 is a view similar to FIG. 25 illustrating a second step of collapsing the collapsible detection antenna.

In still another embodiment illustrated in FIGS. 25-26, the step of collapsing may include using the retaining member 54 in the form of two more magnets with at least one in the handle 38 that are then used to hold the antenna assembly 18 in place along the width. In another embodiment, the retaining member 54 may be magnets mounted on a lever (not shown) inside the housing 19 that would be connected to a button (not shown) that could be activated by the user to release the magnets when the antenna assembly 18 is deployed. In another embodiment, the user could manually release the antenna assembly 18 from the magnets. It should be appreciated that the magnets have no effect on the electromagnetic field. It should also be appreciated that the spring steel inside the structural member 28 would do the job of quickly returning the antenna assembly 18 to its circular shape for use.

Figure 27:
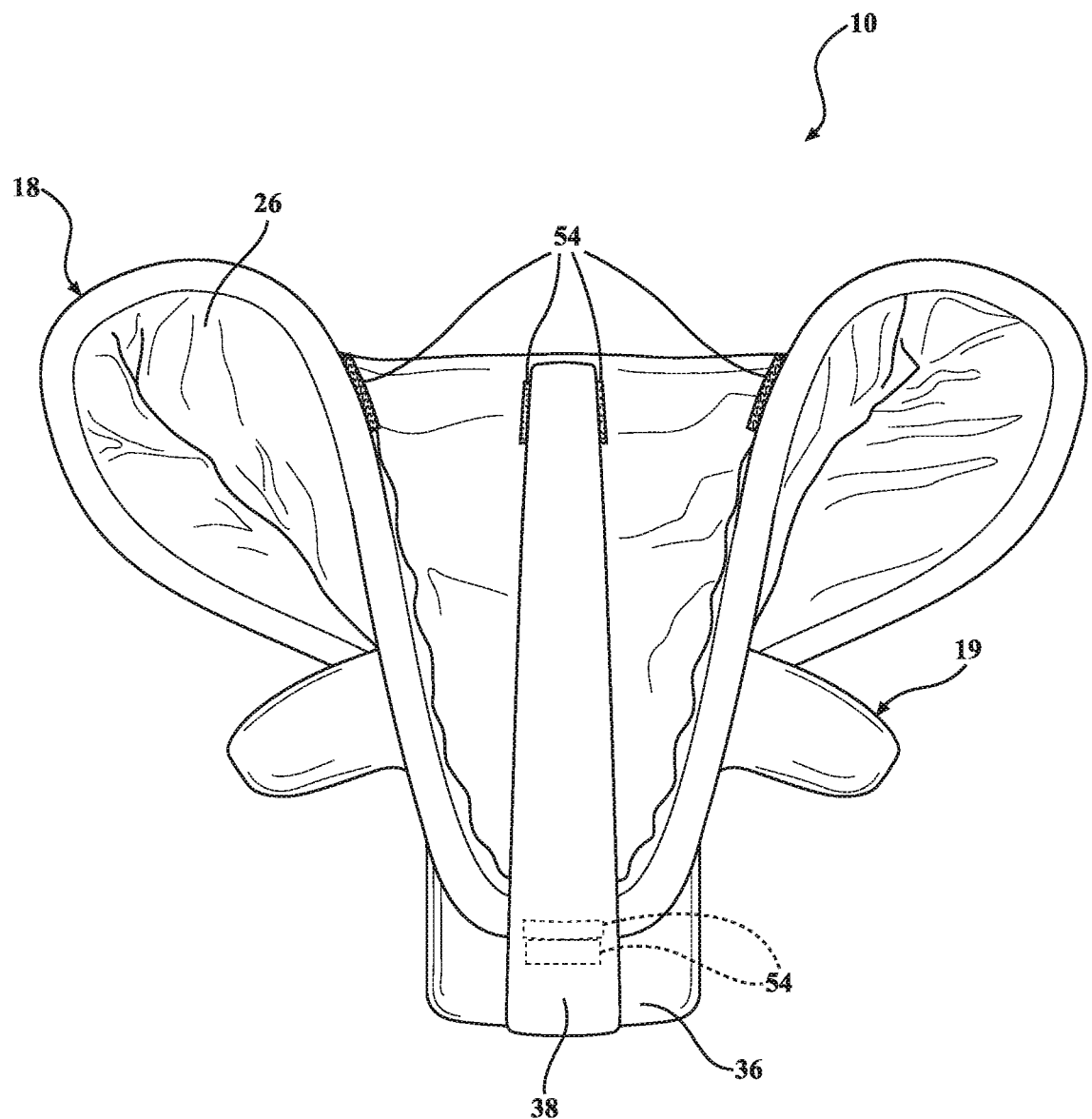
FIG. 27 is a view similar to FIG. 25 illustrating a third step of collapsing the collapsible detection antenna.
Figure 28:
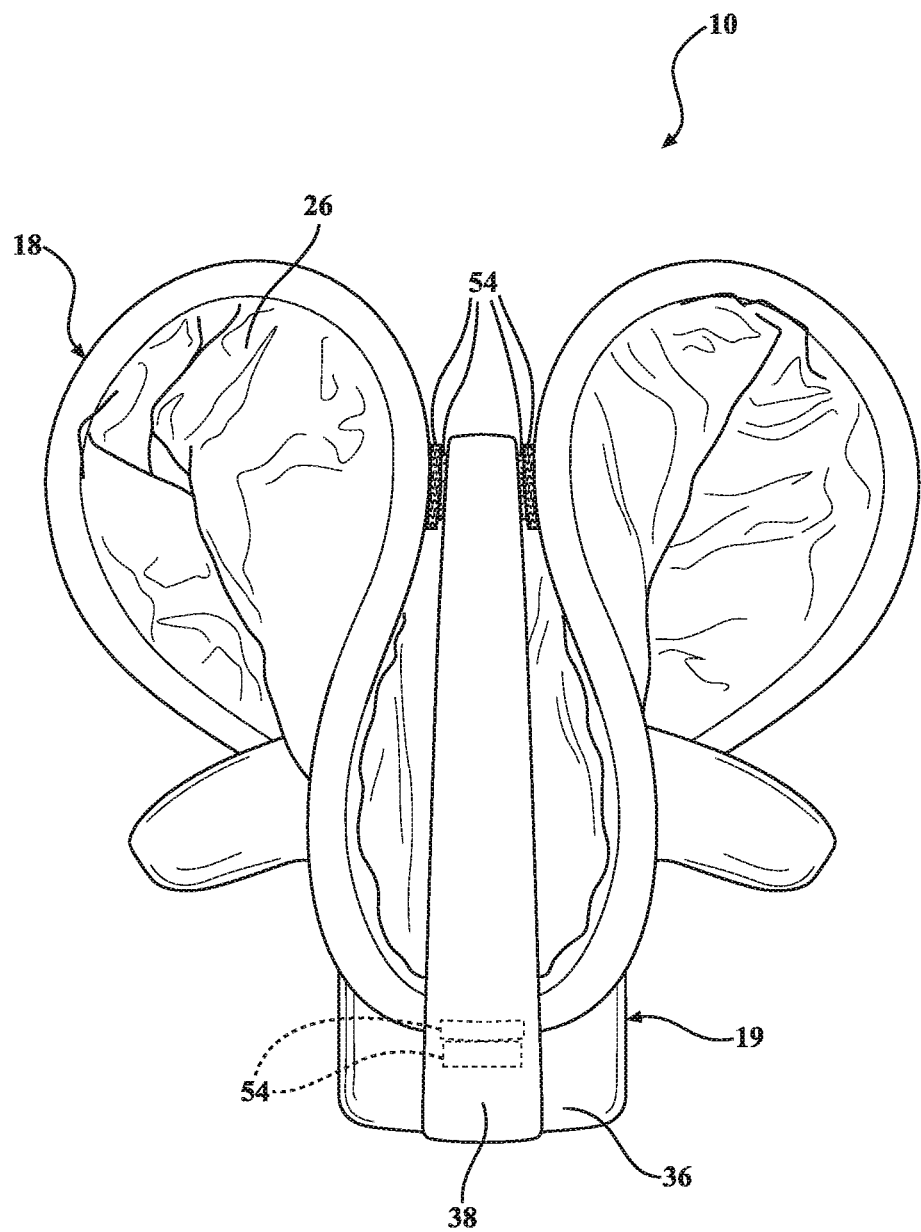
FIG. 28 is a view similar to FIG. 25 illustrating a fourth step of collapsing the collapsible detection antenna.

In yet another embodiment illustrated in FIGS. 27 and 28, the step of collapsing may be using the retaining member 54 as a hook and/or loop material to maintain the shape of the antenna assembly 18 in different collapsed configurations.

Figure 29:
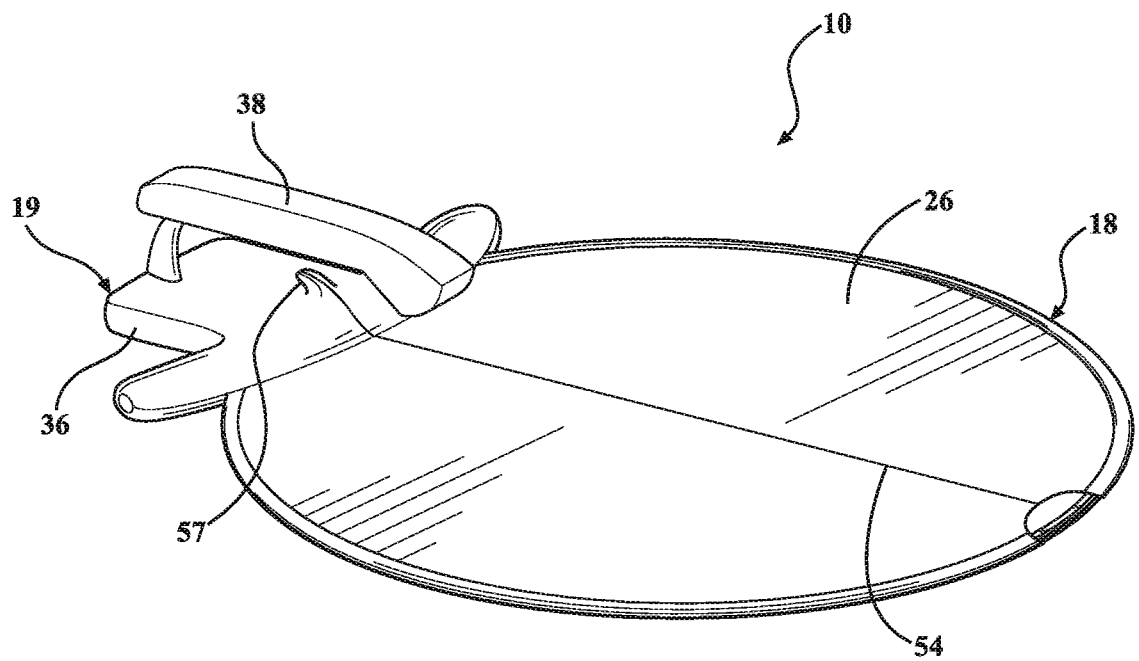
FIG. 29 is a view of a further embodiment of a method, according to the present invention, of collapsing the collapsible detection antenna of FIG. 1 illustrating a first step of collapsing the collapsible detection antenna.
Figure 30:
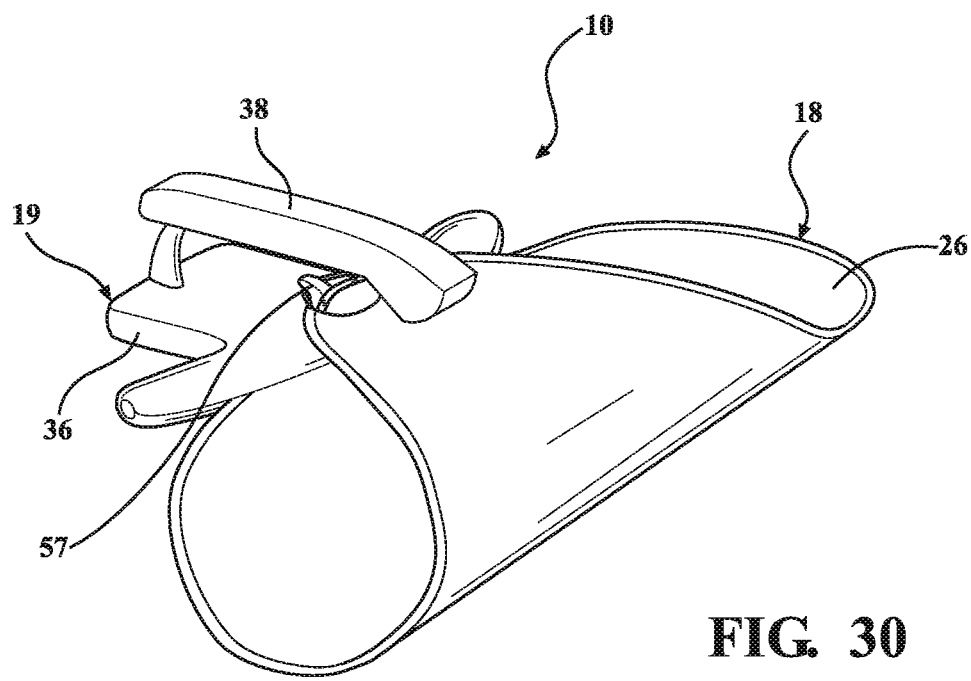
FIG. 30 is a view similar to FIG. 29 illustrating a second step of collapsing the collapsible detection antenna.

In yet another embodiment illustrated in FIGS. 29 and 30, the step of collapsing may be using the retaining member 54 in the form of at least one or more strings attached to the antenna assembly 18. As illustrated in FIG. 29, the antenna assembly 18 is in the deployed configuration and the method includes the step of pulling the at least one string to collapse the antenna assembly 18 as illustrated in FIG. 30. In this embodiment, one or more metal or synthetic strings would be attached to the circumference of the antenna assembly 18 and pulled by a lever or revolving handle (not shown). Releasing the lever would return the antenna assembly 18 to the circular shape due to the tendency of the spring steel of the structural member 28 to go back to its circular shape. In another embodiment, these strings may span transversely through the antenna loop 20 and attach at specific control points around the perimeter. As illustrated in FIG. 30, the method may include the step of retaining the antenna assembly 18 in the collapsed configuration. When the user wants to retract the antenna assembly 18, a tensioning device 57 such as a cord or knob may be attached to the housing 19 and/or strings and is activated to increase tension and thus reduce the footprint of the antenna assembly 18. This knob can be fully geared or with ratcheting motion. It should be appreciated that one additional benefit of using strings is the ability to control the inherent sagging of the spring steel of the structural member 28 in the lateral direction by holding the perimeter in tension relative to the rigid housing 19.

In another embodiment illustrated in FIGS. 31 and 32, the step of collapsing may be using the retaining member 54 in the form of one or more zippers added to the circumference of the antenna assembly 18 that would aid the collapsing and storage. As illustrated in FIG. 31 the antenna assembly 18 is in the deployed configuration. As illustrated in FIG. 32, the method includes collapsing the antenna assembly 18 to a much more compact size approximately 3 times smaller in diameter and 9 times smaller in surface area.

In still another embodiment illustrated in FIGS. 11 and 20, the collapsing may include using the retaining member 54 in the form of an enclosure. In one embodiment, the enclosure may be attached to the housing 19. The method includes the step of pushing the antenna assembly 18 into the enclosure to collapse the antenna assembly 18. Different enclosures with different shapes and built-in restraining features could be used to shape the antenna assembly 18 into a compact size when the antenna assembly 18 is pushed into the enclosure. This embodiment may be used with or without any combination of the collapsing methods described above. One such example may be magnets or zippers to collapse the antenna assembly 18 in the transverse directions where it is then inserted into a specially formed sleeve or enclosure to collapse further in the radial direction as illustrated in FIGS. 31 and 32. It should be appreciated that the enclosure could be permanently located on a support structure such as the housing 19 or be completely free standing accessory.

The method may include the step of positioning a sterile drape (not shown) over the antenna assembly 18 while the antenna assembly 18 is in the collapsed configuration. When the collapsible detection antenna 10 needs to be used to search for the electromagnetic tag 12 in a sterile field, it will be placed within a sterile sleeve with one end closed. In one embodiment, the sterile sleeve is made of a polyethylene film and has a closure, such as re-applicable tape, to secure the sleeve around the antenna assembly 18 and the wire 22 (FIG. 1) connecting the collapsible detection antenna 10 to the RFID reader (not shown). The collapsible detection antenna 10 could make it easier for healthcare workers to apply the drape. A sterile drape is typically packaged in a folded manner so that one sterile user can insert the antenna assembly 18 through the open end, without touching the exterior of the sleeve that is held by a sterile user. The form of the folded drape can be maintained by adhesives, tapes or other closure or fastening mechanisms. As the antenna assembly 18 is inserted, the sleeve unfolds, until the antenna assembly 18 is at the closed end of the sleeve and then the sterile user will grasp the portion of the sterile sleeve that contains the antenna assembly 18. In one embodiment, the sterile sleeves are typically at least 8 feet long. With the collapsible detection antenna 10, the user may deploy the antenna assembly 18 from the collapsed configuration to the deployed configuration when the antenna assembly 18 is at least partially within the drape to help unfold the drape. In order to minimize bulkiness and prevent contact with non-sterile objects, a user will typically wrap tape or other fasteners around the drape and the wire 22 that connects the collapsible detection antenna 10 to the RFID reader. With the collapsible detection antenna 10, the drape could potentially have a wide end section in which the drape can be fully opened and a narrower leading end that reduces the bulkiness of the drape.

Figure 35A:
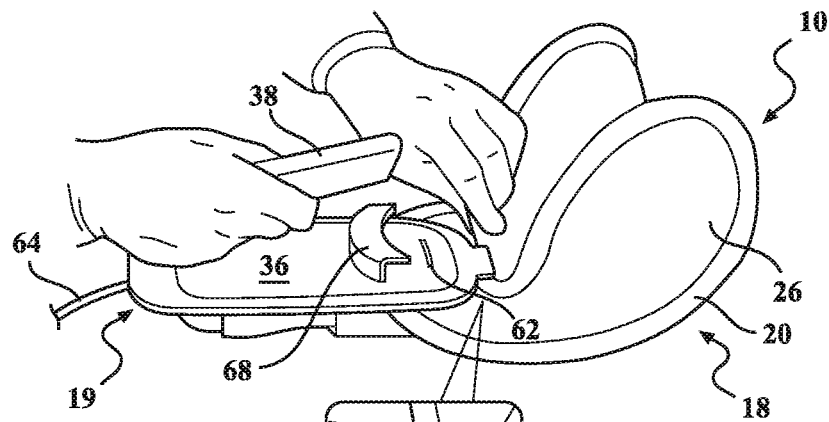
FIG. 35 is yet still another embodiment, according to the present invention, of the collapsible detection antenna of FIG. 1 illustrating a series of steps A-C of collapsing the collapsible detection antenna.
Figure 35B:
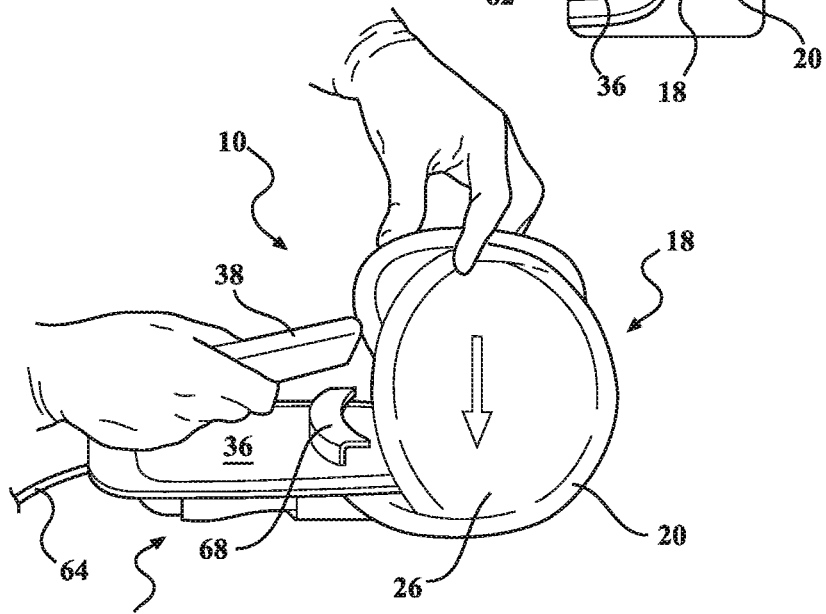
Figure 35C:
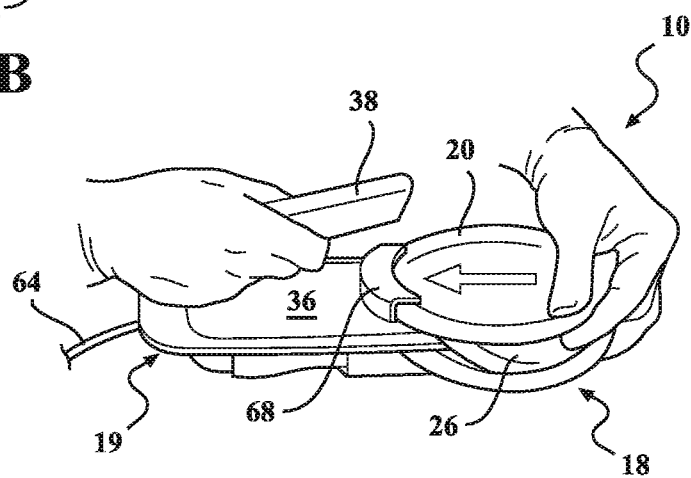

In a still yet further embodiment illustrated in FIGS. 35-36, a method of collapsing the antenna assembly 18 is shown. As illustrated in FIG. 35, the method may include a series of steps A-C of collapsing the antenna assembly 18. As illustrated in FIG. 35A, the method includes the steps of positioning the front of the antenna assembly 18 under the tab 66, which in this embodiment is a flat extension from the housing 19. As illustrated in FIG. 35B, the method includes the steps of pushing or pulling the outward portions of the antenna assembly 18 inwardly. As illustrated in FIG. 35C, the method includes the steps of placing a portion of the antenna assembly 18 in the holding member 68.

Figure 38:
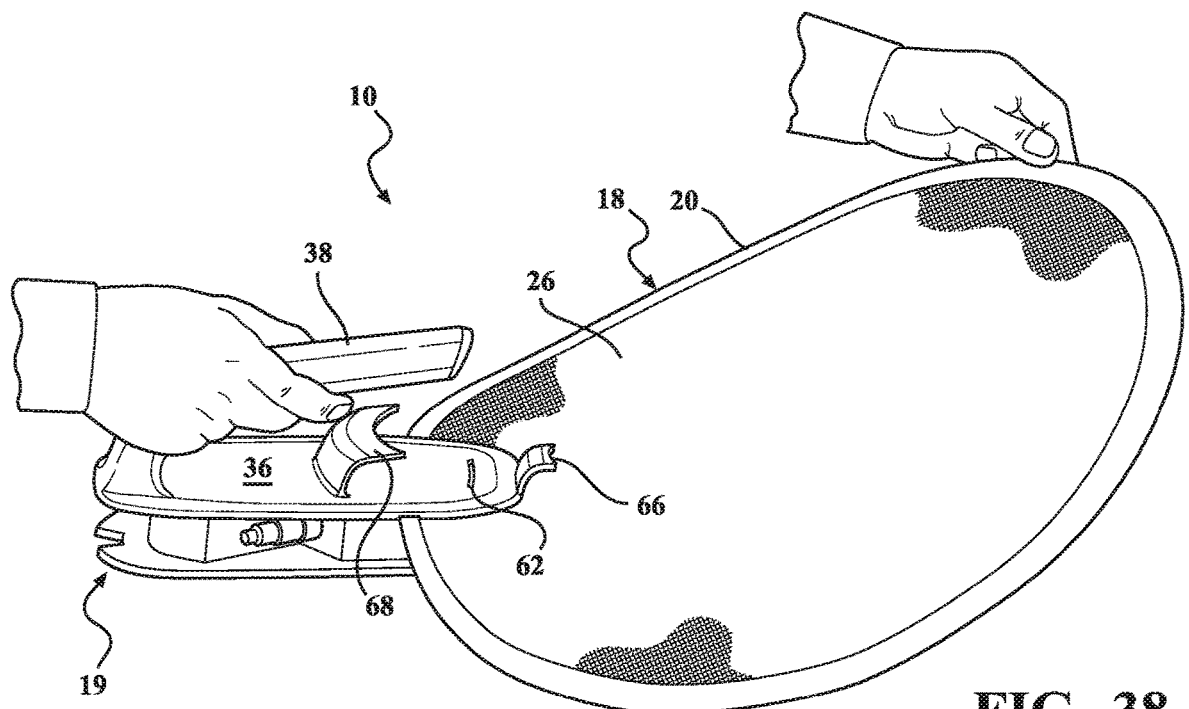
Figure 39:
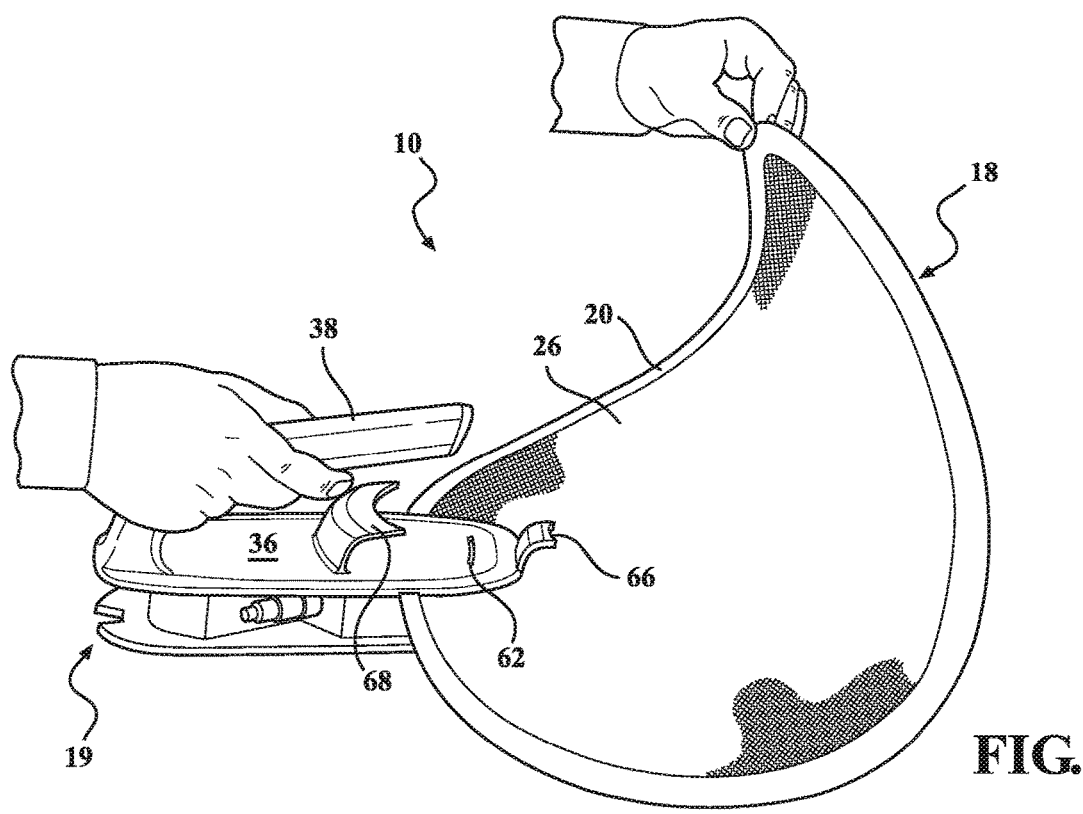
Figure 40:
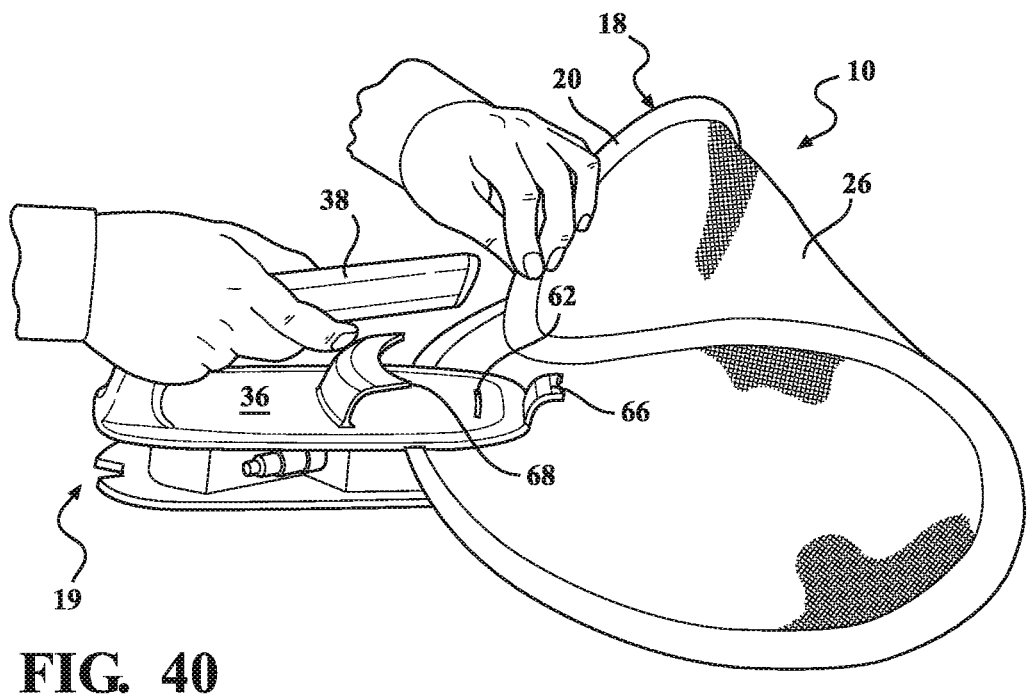
Figure 41:
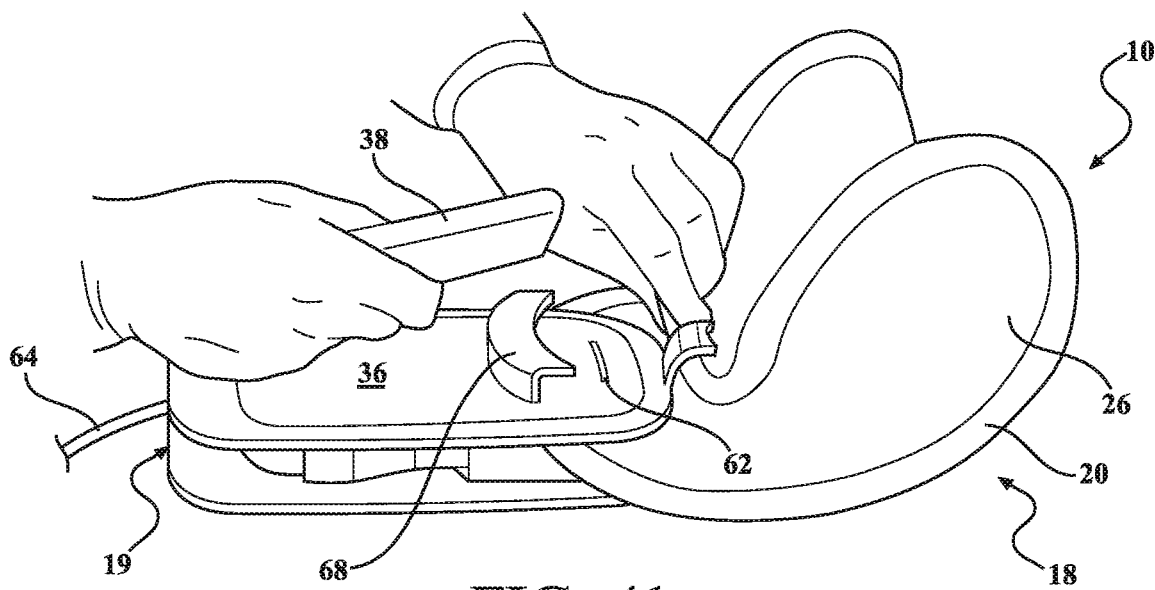
Figure 42:
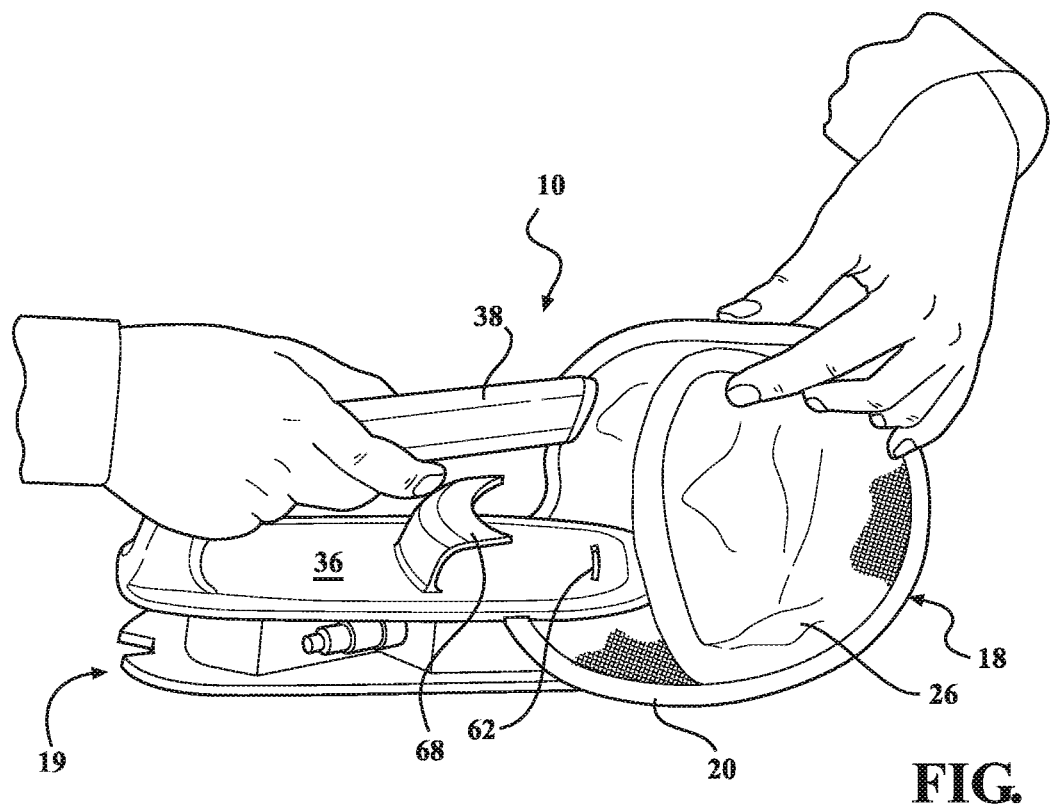
Figure 43:
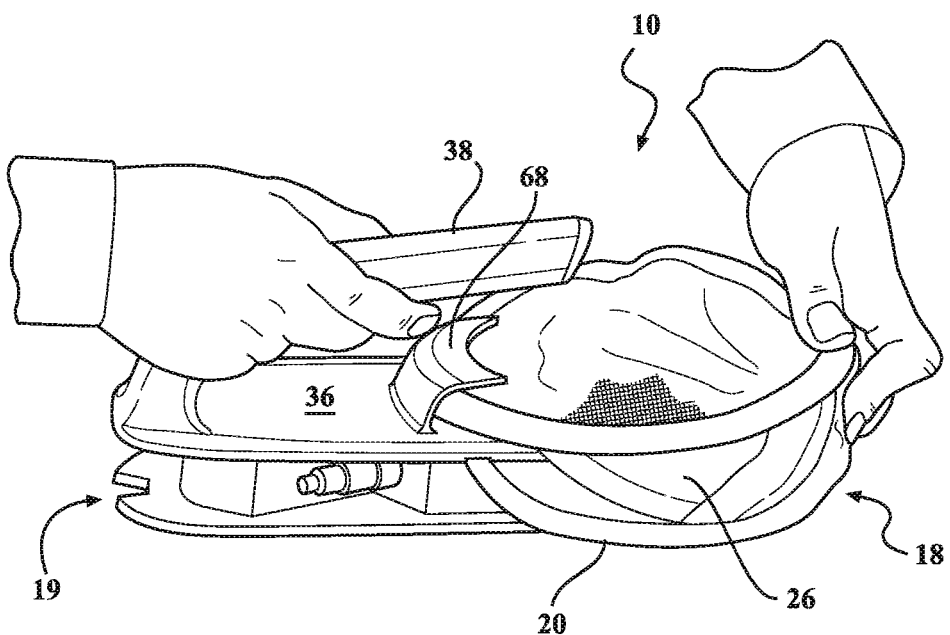
Figure 44:
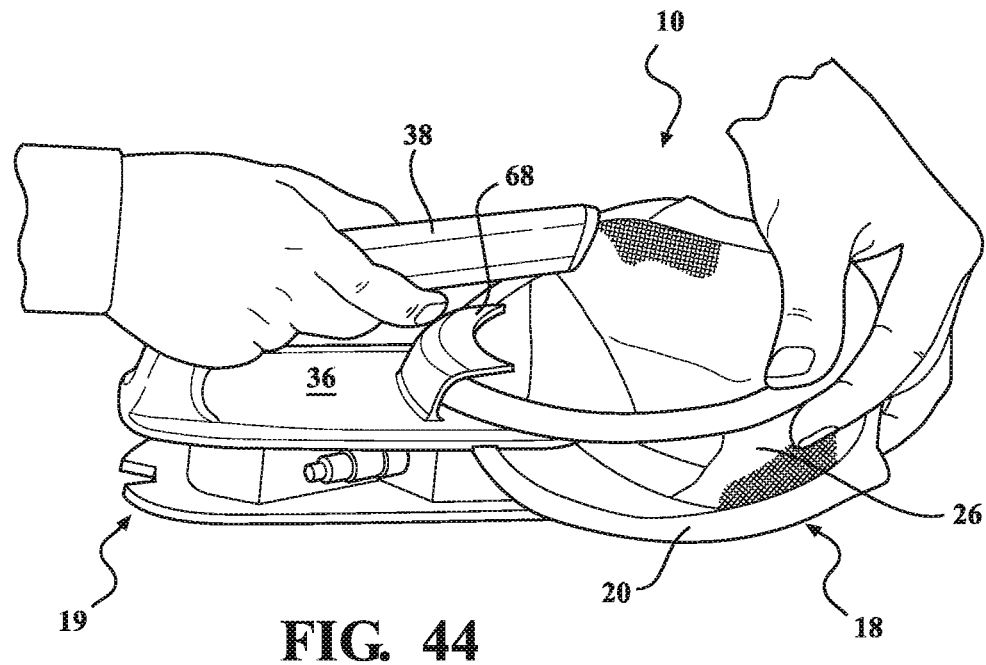
Figure 45:
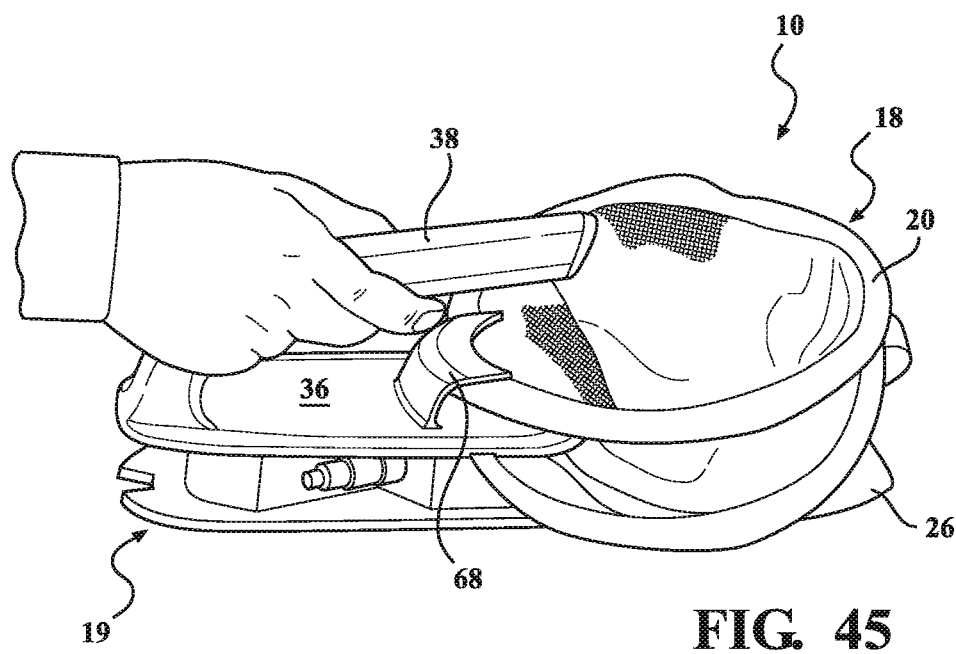

FIGS. 37-44 illustrate more detailed steps of collapsing the antenna assembly 18. As illustrated in FIG. 37, the antenna assembly 18 is shown in the deployed configuration. As illustrated in FIGS. 38-40, the method includes the steps of grasping the antenna assembly 18 by the hand of the user at the front or distal edge (away from the handle 38) and pulling the antenna assembly 18 toward the handle 38. As illustrated in FIG. 41, the method includes the steps of positioning the front of the antenna assembly 18 under the tab 66, which in this embodiment is a curved extension from housing 19 to aid in the proper locating of the antenna assembly 18. As illustrated in FIG. 42, the method includes the step of pushing or pulling the outward portions of the antenna assembly 18 inwardly. As illustrated in FIGS. 43-45, the method includes the steps of placing a portion of the antenna assembly 18 in the holding member 68. It should be appreciated that the antenna assembly 18 is collapsed to a much more compact size approximately 3 times smaller in diameter and 9 times smaller in surface area in the collapsed configuration.

Figure 46:
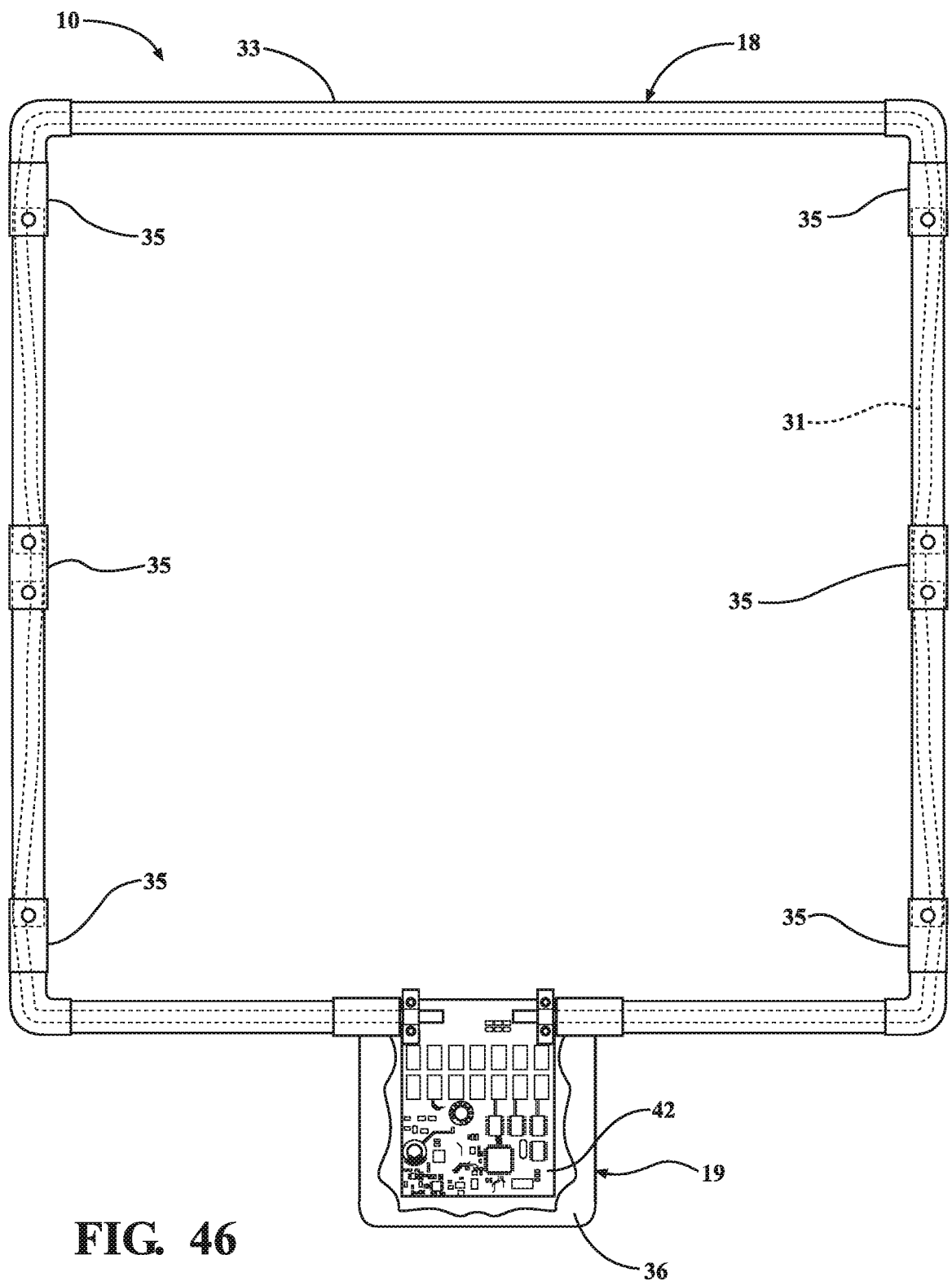
FIG. 46 is a plan view of still yet another embodiment, according to the present invention, of the collapsible detection antenna of FIG. 1 illustrating a deployed configuration.
Figure 47:
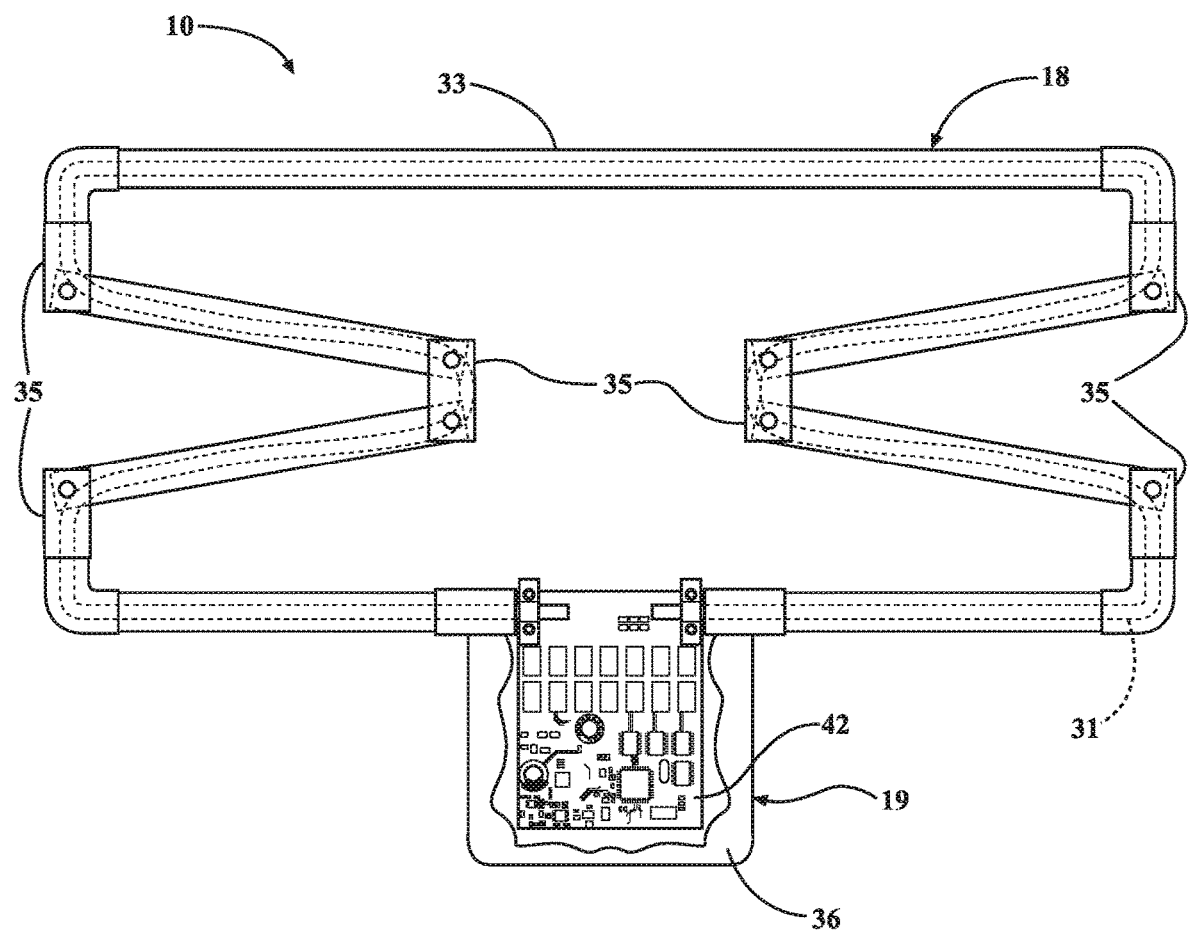
FIG. 47 is a view similar to FIG. 46 illustrating a collapsed configuration.

In another embodiment illustrated in FIGS. 46 and 47, the collapsible detection antenna 10 may include a conductor 31 for carrying the RF wave and a housing 33. In this embodiment, the conductor 31 is passed through the housing 33 and the housing 33 has multiple joints 35 that would help bend the conductor 31 into a compact shape. It should be appreciated that the collapsible detection antenna 10 is illustrated in a deployed configuration in FIG. 45 and in a collapsed condition in FIG. 46.

In the embodiment of FIGS. 46 and 47, the joints 35 may assume any suitable configuration so long as the joints 35 are capable of assuming multiple positions corresponding to the collapsed and deployed positions. For example, the joints 35 may be detent joints, hinges, friction locks, magnet latches, snapped joints, etc. Any number of joints 35 may be utilized and the joints 35 may be positioned at any suitable location about the length of the conductor 31.

Accordingly, the collapsible detection antenna 10 of the present invention provides a handheld RF antenna loop 20 with capability of collapsing to smaller sizes for easier storage and transportation. The collapsible detection antenna 10 of the present invention could be used in a variety of applications including detection of RFID or electromagnetic tags 12 for surgical articles 14 retained inside a patient's body or misplaced in an operating room 16. In other embodiments, the collapsible detection antenna 10 may be used for detecting items other than the electromagnetic tags 12. The collapsible detection antenna 10 of the present invention allows the antenna assembly 18 to change shape and become compact for storage.

Clause 1: A collapsible detection antenna to detect electromagnetic tags of surgical articles in an operating room, said collapsible detection antenna comprising: an antenna assembly configured to detect the electromagnetic tags, said antenna assembly configured to move between a deployed configuration and a collapsed configuration, wherein, in said deployed configuration, said antenna assembly forms an antenna loop configured to detect the electromagnetic tags, said antenna assembly having a greater detection range in said deployed configuration than in said collapsed configuration, said deployed configuration corresponding to a tuned shape of said antenna assembly sufficient to detect the electromagnetic tags in said deployed configuration.

Clause 2: A collapsible detection antenna as set forth in clause 1, wherein said antenna assembly comprises a loop assembly and a support member coupled to said loop assembly.

Clause 3: A collapsible detection antenna as set forth in clause 2, wherein said support member and said loop assembly are arranged to prevent deformation of said loop assembly in at least one direction to retain a stable shape of said antenna loop when said antenna assembly is in said deployed configuration.

Clause 4: A collapsible detection antenna as set forth in any of clause 2-3, wherein said loop assembly comprises a structural member and a conductor coupled to said structural member.

Clause 5: A collapsible detection antenna as set forth in clause 4, wherein said structural member comprises spring steel.

Clause 6: A collapsible detection antenna as set forth in any of clauses 4-5, wherein said structural member has a rectangular cross-sectional profile.

Clause 7: A collapsible detection antenna as set forth in clause 6, wherein said rectangular cross-sectional profile has a height to width ratio ranging between 20:1 to 5:1.

Clause 8: A collapsible detection antenna as set forth in any of clauses 4-5, wherein said structural member has one of an arcuate cross-sectional profile and a semi-circular cross-sectional profile.

Clause 9: A collapsible detection antenna as set forth in any of clauses 4-8, wherein said conductor is disposed about said structural member and wherein said conductor comprises a braided wire.

Clause 10: A collapsible detection antenna as set forth in any of clauses 2-9, wherein said loop assembly comprises a first layer of electrical insulator disposed between said conductor and said structural member.

Clause 11: A collapsible detection antenna as set forth in clause 10, wherein said loop assembly comprises a second layer of electrical insulation disposed about said conductor.

Clause 12: A collapsible detection antenna as set forth in any of clauses 4-11, further comprising a tuning board in electrical communication with said conductor to generate a detection field to match a frequency range of the electromagnetic tags.

Clause 13: A collapsible detection antenna as set forth in any of clauses 1-12, including a housing coupled to said antenna assembly to support said antenna assembly and configured to be grasped by a user.

Clause 14: A collapsible detection antenna as set forth in clause 13, wherein said housing comprises a handle to be grasped by the user so that said antenna assembly can be moved by the user.

Clause 15: A collapsible detection antenna as set forth in any of clauses 12-14, wherein said structural member has a first end and a second end with said first end and said second end coupled to said tuning board.

Clause 16: A collapsible detection antenna as set forth in any of clauses 4-15, wherein said structural member has a first end and a second end, said first end and said second end being discontinuous such that electrical energy cannot be transmitted between said first end and said second end to prevent formation of eddy currents.

Clause 17: A collapsible detection antenna as set forth in any of clauses 4-16, wherein said structural member comprises a creep-resistant material.

Clause 18: A collapsible detection antenna as set forth in clause 17 wherein said creep resistant material is selected from the group consisting of PEEK, nitinol, or combinations thereof.

Clause 19: A collapsible detection antenna as set forth in any of clauses 2-18, wherein said support member spans an interior chord of said antenna loop.

Clause 20: A collapsible detection antenna as set forth in clause 2-19, wherein said support member is attached to itself about a circumference to provide a channel for said loop assembly to pass through.

Clause 21: A collapsible detection antenna as set forth in any of clauses 2-20, wherein said support member comprises one from the group comprising a woven fabric, non-woven fabric, thermoplastic film, and combinations thereof.

Clause 22: A collapsible detection antenna as set forth in any of clauses 2-21, wherein said support member spans 25% to 100% of an interior area of said antenna loop.

Clause 23: A collapsible detection antenna as set forth in any of clauses 1-22, further comprising a retaining member to retain said antenna assembly in said collapsed configuration.

Clause 24: A collapsible detection antenna as set forth in clause 23, wherein said retaining member comprises a zipper.

Clause 25: A collapsible detection antenna as set forth in clause 23, wherein said retaining member comprises a hook material or a loop material.

Clause 26: A collapsible detection antenna as set forth in clause 23, wherein said retaining member comprises a string.

Clause 27: A collapsible detection antenna as set forth in clause 23, wherein said retaining member comprises an enclosure to allow said antenna assembly to be disposed therein to collapse said antenna assembly.

Clause 28: A collapsible detection antenna as set forth in any of clauses 13-14, further comprising an emitter coupled to said housing to emit at least one of an audible tone and visual tone upon detection of the electromagnetic tags.

Clause 29: A collapsible detection antenna as set forth in any of clauses 13-14, and 28, further comprising a feedback module coupled to said housing to provide haptic feedback upon detection of the electromagnetic tags.

Clause 30: A collapsible detection antenna to detect electromagnetic tags of surgical articles in an operating room, said collapsible detection antenna comprising: an antenna assembly configured to detect the electromagnetic tags, said antenna assembly configured to move between a deployed configuration and a collapsed configuration, wherein, in said deployed configuration, said antenna assembly forms an antenna loop configured to detect the electromagnetic tags, said antenna assembly having a greater detection range in said deployed configuration than in said collapsed configuration, and said deployed configuration corresponding to a tuned shape of said antenna assembly sufficient to detect the electromagnetic tags in said deployed configuration; wherein said antenna assembly comprises a loop assembly and a fabric coupled to said loop assembly, said fabric arranged to prevent deformation of said loop assembly in at least one direction to retain a stable shape of said antenna loop when said antenna assembly is in said deployed configuration; and a housing coupled to said antenna assembly.

Clause 31: A collapsible detection antenna as set forth in clause 30, wherein said fabric spans an interior area of said antenna loop to provide stability to prevent said loop assembly from radial outward movement.

Clause 32: A method of collapsing a collapsible detection antenna used to detect electromagnetic tags of surgical articles, said method comprising the steps of: providing an antenna assembly configured to detect the electromagnetic tags, the antenna assembly configured to be resilient and move between a deployed configuration and a collapsed configuration, wherein, in the deployed configuration, the antenna assembly forms an antenna loop configured to detect the electromagnetic tags, the antenna assembly having a greater detection range in the deployed configuration than in the collapsed configuration, the deployed configuration corresponding to a tuned shape of the antenna assembly sufficient to detect the electromagnetic tags in the deployed configuration; and collapsing the antenna assembly from the deployed configuration to the collapsed configuration.

Clause 33: A method as set forth in clause 32, wherein the step of collapsing further comprises using a twisting motion to collapse the antenna assembly.

Clause 34: A method as set forth in clause 33, wherein the step of using a twisting motion comprises using a 360 degree twisting motion.

Clause 35: A method as set forth in clause 32, including the step of providing a housing coupled to the antenna assembly to support the antenna assembly and configured to be grasped by a user.

Clause 36: A method as set forth in clause 35, wherein the step of collapsing further comprises grasping the antenna assembly by the user at a distal end from the housing and pulling toward the handle to collapse the antenna assembly.

Clause 37: A method as set forth in clause 32, wherein the step of collapsing further comprises using a magnet coupled to the housing to attract the antenna assembly toward the housing.

Clause 38: A method as set forth in clause 32, wherein the step of collapsing further comprises using a string attached to the antenna assembly and pulling the string toward the housing to collapse the antenna assembly.

Clause 39: A method as set forth in clause 32, wherein the step of collapsing further comprises providing an enclosure and pushing the antenna assembly into the enclosure to collapse the antenna assembly.

Clause 40: A method as set forth in any of the clauses 32-39, including the step of retaining the antenna assembly in the collapsed configuration.

Clause 41: A method as set forth in any of the clauses 32-40, including the step of positioning a sterile drape over the antenna assembly while the antenna assembly is in the collapsed configuration.

Clause 42: A collapsible detection antenna to detect electromagnetic tags of surgical articles in an operating room, said collapsible detection antenna comprising: an antenna assembly configured to detect the electromagnetic tags, said antenna assembly configured to move between a deployed configuration and a collapsed configuration, wherein, in said deployed configuration, said antenna assembly forms an antenna loop configured to detect the electromagnetic tags, said antenna assembly having a greater detection range in said deployed configuration than in said collapsed configuration, said collapsible detection antenna is configured to detect electromagnetic tags having a frequency ranging from 3 to 30 MHz.

Clause 43. A collapsible detection antenna and method as disclosed and described herein, including equivalents not specifically recited herein.

The present invention has been described in an illustrative manner. It is to be understood that the terminology, which has been used, is intended to be in the nature of words of description rather than of limitation. Many modifications and variations of the present invention are possible in light of the above teachings. Therefore, the present invention may be practiced other than as specifically described.

What is claimed is:

1. An apparatus for detection of electromagnetic tags of surgical articles in an operating room, the apparatus comprising:
   a housing comprising a handle configured to be grasped by a user; and
   an antenna assembly coupled to the housing and comprising a loop assembly, wherein the loop assembly comprises a conductor and a structural member enclosed inside the conductor,
   wherein the antenna assembly is configured to move from a collapsed configuration to a deployed configuration in which the antenna assembly forms an antenna loop configured to detect the electromagnetic tags and has a greater detection range in the deployed configuration than in the collapsed configuration.

2. The apparatus of claim 1, wherein the loop assembly further comprises an electrical insulator disposed between the conductor and the structural member.

3. The apparatus of claim 1, wherein the loop assembly further comprises another layer of electrical insulator disposed about the conductor.

4. The apparatus of claim 1, further comprises a tuning board disposed within the housing and in electrical communication with the conductor, wherein the tuning board is configured to generate a detection field to match a frequency range of the electromagnetic tags.

5. The apparatus of claim 4, wherein the structural member comprises first and second ends coupled to the tuning board.

6. The apparatus of claim 1, further comprising a retaining member coupled to the housing and configured to retain the antenna assembly in the collapsed configuration.

7. The apparatus of claim 6, wherein the retaining member comprises an enclosure within which the antenna assembly is configured to be disposed in the collapsed configuration.

8. The apparatus of claim 1, wherein the antenna assembly further comprises a support member coupled to the loop assembly, wherein the support member and the loop assembly are arranged to stabilize a shape of the antenna loop with the antenna assembly in the deployed configuration.

9. The apparatus of claim 8, wherein the support member is attached to itself about a circumference to provide a channel for the loop assembly to pass through.

10. The apparatus of claim 8, wherein the support member spans 25% to 100% of an interior area of the antenna loop.

11. The apparatus of claim 1, wherein the structural member comprises a material selected from the group consisting of spring steel, a creep-resistant material, PPEK, nitinol, or combinations thereof.

12. The apparatus of claim 1, wherein the structural member has a rectangular cross-section having a height to width ratio ranging between 20:1 to 5:1.

13. The apparatus of claim 1, wherein the structural member comprises a first end and a second end, the first end and the second end being discontinuous such that electrical energy cannot be transmitted between the first end and the second end to prevent formation of eddy currents.

14. The apparatus of claim 1, further comprising an emitter coupled to the housing and configured to emit at least one of an audible tone and a visual tone upon detection of the electromagnetic tags.

15. The apparatus of claim 1, further comprising a feedback module coupled to the housing and configured to provide haptic feedback upon detection of the electromagnetic tags.

16. An apparatus for detection of electromagnetic tags of surgical articles in an operating room, the apparatus comprising:
   a housing comprising a handle configured to be grasped by a user; and
   an antenna assembly coupled to the housing and comprising a loop assembly, wherein the loop assembly comprises a conductor and a structural member enclosed inside the conductor, wherein the antenna assembly is configured to move from a collapsed configuration to a deployed configuration in which the antenna assembly forms an antenna loop configured to detect the electromagnetic tags; and
   a tuning board coupled to the conductor and configured to emit a signal that matches a resonant frequency of the antenna assembly in the deployed configuration, wherein the signal does not match the resonant frequency of the antenna assembly in the collapsed configuration.

17. The apparatus of claim 16, wherein the structural member comprises first and second ends each coupled to the tuning board.

18. An apparatus for detection of electromagnetic tags of surgical articles in an operating room, the apparatus comprising:
   a housing comprising a handle configured to be grasped by a user; and
   an antenna assembly coupled to the housing and comprising a loop assembly, wherein the loop assembly comprises a structural member, a conductor, an insulator.

* * * * *

UNITED STATES PATENT AND TRADEMARK OFFICE
CERTIFICATE OF CORRECTION

PATENT NO. : 11,759,263 B2
APPLICATION NO. : 16/337059
DATED : September 19, 2023
INVENTOR(S) : Fazel Yavari et al.

It is certified that error appears in the above-identified patent and that said Letters Patent is hereby corrected as shown below:

In the Claims

In Column 18, Line 64 (Claim 18):
Please replace "comprises a structural member, a conductor, an insulator"
With -- "comprises a structural member, a conductor, an insulator surrounding the structural member and the conductor, and a support member surrounding the insulator, wherein the antenna assembly is configured to move from a collapsed configuration to a deployed configuration in which the antenna assembly forms an antenna loop configured to detect the electromagnetic tags and has a greater detection range in the deployed configuration than in the collapsed configuration." --

Signed and Sealed this
Twenty-eighth Day of May, 2024

Katherine Kelly Vidal
*Director of the United States Patent and Trademark Office*